(12) United States Patent
Bonham et al.

(10) Patent No.: US 7,608,620 B2
(45) Date of Patent: *Oct. 27, 2009

(54) LPAAT-β INHIBITORS AND USES THEREOF

(75) Inventors: Lynn Bonham, Seattle, WA (US);
Baoqing Gong, Shoreline, WA (US);
Robert E Finney, Shoreline, WA (US);
David M Hollenback, Seattle, WA (US);
J Peter Klein, Vashon, WA (US); David W Leung, Mercer Island, WA (US);
Scott A Shaffer, Seattle, WA (US);
Norina M Tang, Ann Arbor, MI (US);
John Tulinsky, Seattle, WA (US);
Thayer H White, Bellevue, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/601,513

(22) Filed: Nov. 16, 2006

(65) Prior Publication Data
US 2007/0072856 A1 Mar. 29, 2007

Related U.S. Application Data

(60) Continuation of application No. 11/224,340, filed on Sep. 12, 2005, now Pat. No. 7,199,238, which is a division of application No. 10/712,900, filed on Nov. 13, 2003, now Pat. No. 7,064,125, which is a continuation-in-part of application No. 10/236,084, filed on Sep. 6, 2002, now abandoned, which is a continuation of application No. 09/984,888, filed on Oct. 31, 2001, now abandoned.

(60) Provisional application No. 60/244,195, filed on Oct. 31, 2000.

(51) Int. Cl.
C07D 251/52 (2006.01)
C07D 251/38 (2006.01)
A61K 31/53 (2006.01)
A61P 35/00 (2006.01)

(52) U.S. Cl. .................. 514/245; 544/197; 544/198; 544/205; 544/206; 544/207; 544/208; 544/209; 544/210

(58) Field of Classification Search .............. 544/204, 544/208, 209, 197, 198, 205, 206, 207, 210, 544/199; 514/245
See application file for complete search history.

(56) References Cited

U.S. PATENT DOCUMENTS

| 3,625,979 | A | * | 12/1971 | Heimberger | ............ | 544/113 |
| 5,702,717 | A |   | 12/1997 | Cha et al. | ............ | 424/425 |
| 6,288,228 | B1 |  | 9/2001  | Henkin et al. | ......... | 544/197 |
| 7,064,125 | B2 | * | 6/2006 | Gong et al. | ............ | 514/241 |
| 2002/0065270 | A1 |  | 5/2002 | Moriarty et al. | ....... | 514/218 |

FOREIGN PATENT DOCUMENTS

| DE | 2104232 A | 9/1971 |
| DE | 2311237 A | 9/1974 |
| DE | 2833582 A | 2/1979 |
| EP | 084 767 A | 8/1983 |
| EP | 096 189 A | 12/1983 |
| JP | 01-261307 A | 6/1989 |
| JP | 11-158073 A | 6/1999 |
| WO | WO 91/11465 | 8/1991 |
| WO | WO 93/17002 | 9/1993 |
| WO | WO 96/04281 | 2/1996 |
| WO | WO 00/43369 | 7/2000 |
| WO | WO 01/47897 | 7/2001 |

OTHER PUBLICATIONS

Cuthbertson et al., Journal of Chemical Society, 561-564, 1948. CA 42: 32078.*
Britten and Kohne, "Repeated Sequences in DNA," *Science* 161(3841): 529-540, Aug. 9, 1968.
Bursten et al., "Interleukin-1 Rapidly Stimulates Lysophosphatidate Acyltransferase and Phosphatidate Phosphohydrolase Activities in Human Mesangial Cells," *Journal of Biological Chemistry* 266(31): 20732-20743, Nov. 5, 1991.
Bursten et al., "Lipid A activation of glomerular mesangial cells: mimicry of the bioactive lipid, phosphatidic acid," *American Journal of Physiology* 262(2): C328-C338, Feb. 1992.
Curd et al., *J. Chem. Soc.* 160-162, 1947. Database Crossfire Beilstein, Database Accession No. 49402.
Cuthbertson et al., *J. Chem. Soc.*, 561-563, 1948. Database Crossfire Beilstein, Database Accession No. 35104, 284744.
Degussa, ZA 6707089, 1968. Chemical Abstracts 70:57905, 1969. And Database Crossfire Beilstein, Database Accession No. 1158601.
Eberhardt et al., "Human Lysophosphatidic Acid Acyltransferase," *Journal of Biological Chemistry* 272(32): 20299-20305, Aug. 8, 1997.
English, D., "Phosphatidic acid: A lipid messenger involved in intracellular and extracellular signaling," *Cell Signal* 8(5): 341-347, 1996.
Fong and Engleman, "Dendritic Cells in Cancer Immunotherapy," *Annual Review of Immunology* 18: 245-273, 2000.
Freiberg et al., *J. Prakt. Chem.* 327(3): 471-478, 1985. Chemical Abstracts 104:68822.
Goi et al., *Yuki Gosei Kagaku Kyokaishi* 18: 332-336, 1960. Database Crossfire Beilstein, Database Accession No. 895595.
Hoess and Abremski, "The Cre-*lox* Recombination System," *Nucleic Acids and Molecular Biology* 4: 99-109, 1990.
Imamura et al, "Induction of in vitro tumor cell invasion of cellular monolayers by lysophosphatidic acid or phospholipase D," *Biochemical and Biophysical Research Communications* 193(2): 497-503, Jun. 15, 1993.
Kester, M., "Platelet-Activating Factor Stimulates Phosphatidic Acid Formation in Cultured Rat Mesangial Cells: Roles of Phospholipase D, Diglyceride Kinase, and De Novo Phospholipid Synthesis," *Journal of Cellular Physiology* 156: 317-325, 1993.

(Continued)

*Primary Examiner*—Venkataraman Balasubramanian
(74) *Attorney, Agent, or Firm*—Seed IP Law Group PLLC

(57) ABSTRACT

The invention relates to triazines and the use thereof to inhibit lysophosphatidic acid acyltransferase β (LPAAT-β) activity. The invention further relates to methods of treating cancer using said triazines. The invention also relates to methods for screening for LPAAT-β activity.

8 Claims, 21 Drawing Sheets

OTHER PUBLICATIONS

Kim et al., *Journal of the Korean Chemical Society 42*(1): 118-121, 1998. Chemical Abstracts 128:282822.

Kim et al., *Journal of the Korean Chemical Society 43*(4): 497-499, 1999. Chemical Abstracts 131:286468.

Köhler and Milstein, "Continuous cultures of fused cells secreting antibody of predefined specificity," *Nature 256*: 495-497, Aug. 7, 1975.

Kotova-kilot et al., *TR. Mosk Khim.-Tekhnol. Inst. 61*: 157-159, 1970. Chemical Abstracts 73:98911.

Kume and Shimizu, "cDNA Cloning and Expression of Murine 1-Acyl-*sn*-glycerol-3-phosphate Acyltransferase," *Biochemical and Biophysical Research Communications 237*(3): 663-666, Aug. 28, 1997.

Langalia et al., *J. Indian Chem. Soc. 59*(9): 1099-1101, 1977. Chemical Abstracts 98:89321.

Laurent et al., Justus Liebigs Ann. Chem 60: 846, 1970. Database Crossfire Beilstein, Database Accession No. 33800.

Leung et al., "Molecular Cloning of Two Alternatively Spliced Forms of Human Phosphatidic Acid Phosphatase cDNAs that Are Differentially Expressed in Normal and Tumor Cells," *DNA and Cell Biology 17*(4): 377-385, Apr. 1998.

Losman et al., "Baboon anti-idiotype antibodies mimic a carcinoembryonic antigen epitope," *Int. J. Cancer 46*(2): 310-314, Aug. 15, 1990.

Martin et al., "Increased concentrations of phosphatidate, diacylglycerol and ceramide in *ras*- and tyrosine kinase (*fps*)-transformed fibroblasts," *Oncogene 14*(13):1571-1580, Apr. 3, 1997.

Metha et al., *J. Inst. Chem*(India) 59(4): 183-185, 1987. Chemical Abstracts 109:6485.

Miller and Rosman, "Improved Retroviral Vectors for Gene Transfer and Expression," *BioTechniques 7*(9): 980-EOA, Oct. 1989.

Moolenaar, W.H., "Lysophosphatidic Acid, a Multifunctional Phospholipid Messenger," *Journal of Biological Chemistry 270*(22): 12949-12952, Jun. 2, 1995.

Neicheva et al., *Journal of Planar Chromatography-Modern TLC 12*(2): 145-149, 1999. Chemical Abstracts 131:28881.

Orlandi et al., "Cloning immunoglobulin variable domains for expression by the polymerase chain reaction," *Proc. Natl. Acad. Sci. USA 86*(10): 3833-3837, May 1989.

Rajnani et al., *J. Inst. Chem.* (India) 49(4): 222-224, 1977. Chemical Abstracts 88:37757.

Rajnani et al., *J. Inst. Chem.*(India) 48(5): 254-255, 1976. Chemical Abstracts 86:189869.

Rao et al., *J. Inst. Chem.*(India) 54(5): 199-200, 1982.

Rizzo et al., "The Recruitment of Raf-1 to Membranes Is Mediated by Direct Interaction with Phosphatidic Acid and Is Independent of Association with Ras," *Journal of Biological Chemistry 275*(31): 23911-23918, Aug. 4, 2000.

Sauer, B., "Inducible Gene Targeting in Mice Using the Cre/*lox* System," *Methods: A Companion to Methods in Enzymology 14*(4): 381-392, Apr. 1998.

Schreurs et al., "Dendritic Cell-Based Vaccines: From Mouse Models to Clinical Cancer Immunotherapy," *Critical Reviews in Oncogenesis 11*(1): 1-17, 2000.

Sharp et al., "Viral DNA in Transformed Cells. I. A Study of the Sequences of Adenovirus 2 DNA in a Line of Transformed Rat Cells Using Specific Fragments of the Viral Genome," *J. Mol. Biol. 86*(4): 709-726, Jul. 15, 1974.

Stamps et al., "A human cDNA sequence with homology to non-mammalian lysophosphatidic acid acyltransferases," *Biochemical Journal 326*:455-461, Sep. 1, 1997.

Sutton, W.D., "A crude nuclease preparation suitable for use in DNA reassociation experiments," *Biochimica et Biophysica Acta 240*(4): 522-531, Jul. 29, 1971.

Unishi et al., *Nippon Kagaku Kaishi 1*:40-44, 1987. Chemical Abstracts 107:134287.

Wakabayashi et al., *Nippon Dojo-Hiryogaku 41*(5): 193-200, 1970. Chemical Abstracts 73:108869.

West et al., "Cloning and Expression of Two Human Lysophosphatidic Acid Acyltransferase cDNAs That Enhance Cytokine-Induced Signaling Responses in Cells," *DNA and Cell Biology 16*(6): 691-701, Jun. 1997.

Wetmur and Davidson, "Kinetics of Renaturation of DNA," *Journal of Molecular Biology 31*(3): 349-370, Feb. 14, 1968.

Xu et al, "Lysophospholipids activate ovarian and breast cancer cells," *Biochemical Journal 309*: 933-940, Aug. 1, 1995.

\* cited by examiner normal adjacent infiltrating ductal carcinoma

Infiltrating adenocarcinoma

Papillary serous cystadenocarcinoma

Papillary serous cystadenocarcinoma

Papillary mucin producing carcinoma adjacent normal adenocarcinoma

| Tissue | Tumor | Normal | Notes |
|---|---|---|---|
| Prostate | 9/9 positive | stroma positive | tumor range + to +++, stroma +++ |
| Breast | 2/12 positive | some endothelium positive glandular epithelium ++ to +++ | tumor range + to +++ |
| Lung | 9/9 positive | alveoli negative some endothelium ++ | tumor range mixed to +++ |
| Ovary | 8/10 positive | stroma mostly negative corpus luteum +++ | tumor range 1 mixed, 8+++ 1 borderline case low |
| Colon | 3/5 positive | endothelium negative some endothelium positive inflammatory cells positive | tumor range mixed/variable focal to +++ 2 tumor-, had stroma +++ |
| Kidney | 5/5 negative | endothelium positive | all tumors +++ vascular endothelium |
| Brain | 5/5 positive | some positivity in neurons | tumor range + to +++ (gliomas) |
| Cervix | 5/5 positive | endothelium negative stroma positive | tumor range + to +++, tumor stroma +++, transition- to +++, hyperplastic area + |
| Bladder | 2/5 positive | urothelium negative submucosal stroma cells +++ | tumors to +++ transition with de-differentiation assoc. stroma more strongly +++ than normal |

FIG. 4E control

Hc2 CRE

+ Ki-ras

Hc2

```
                              SEQUENCE LISTING

<160> NUMBER OF SEQ ID NOS: 5

<210> SEQ ID NO 1
<211> LENGTH: 43
<212> TYPE: DNA
<213> ORGANISM: Artificial Sequence
<220> FEATURE:
<223> OTHER INFORMATION: Primer

<400> SEQUENCE: 1
gcatgaattc aaaggcctac gtcgacatgg agctgtggcc gtg                        43

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
gtcgactcta gactactggg ccggctgcac                                       30

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
tgatatccga agaagatctt atggagctgt ggccgtgtc                             39

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
caggctctag actactgggc cggctgcac                                        29

<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5
cctacgtcga catggaacaa aaattgatat ccgaagaaga tc                         42
```

LPAAT-β INHIBITORS AND USES THEREOF

CROSS REFERENCE TO RELATED APPLICATIONS

This application is a continuation of allowed U.S. patent application Ser. No. 11/224,340 filed Sep. 12, 2005; which application is a divisional of U.S. patent application Ser. No. 10/712,900 filed Nov. 13, 2003, which issued as U.S. Pat. No. 7,064,125; which application is a divisional of U.S. patent application Ser. No. 10/236,084 filed Sep. 06, 2002, abandoned; which application is a continuation of U.S. patent application Ser. No. 09/984,888 filed Oct. 31, 2001, abandoned, which claims priority to U.S. Provisional Application Ser. No. 60/244,195, filed Oct. 31, 2000, abandoned, the disclosures of which are incorporated by reference herein in their entirety.

BACKGROUND OF THE INVENTION

1. Field of the Invention

The invention is in the field of organic and medicinal chemistry. In particular, the invention relates to triazines and the use thereof to inhibit lysophosphatidic acid acyltransferase β (LPAAT-β) activity. The invention further relates to methods of treating cancer using said triazines. The invention also relates to methods for screening for LPAAT-β activity.

2. Related Art

LPAAT catalyzes the acylation of lysophosphatidic acid (LPA) to phosphatidic acid. LPA is the simplest glycerophospholipid, consisting of a glycerol molecule, a phosphate group, and a fatty acyl chain. LPAAT adds a second fatty acyl chain to LPA, producing phosphatidic acid (PA). PA is the precursor molecule for certain phosphoglycerides, such as phosphatidylinositol, and diacylglycerols, which are necessary for the production of other phosphoglycerides, such as phosphatidylcholine, and for triacylglycerols, which are essential biological fuel molecules.

In addition to being a crucial precursor molecule in biosynthetic reactions, LPA has recently been added to the list of intercellular lipid messenger molecules. LPA interacts with G protein-coupled receptors, coupling to various independent effector pathways including inhibition of adenylate cyclase, stimulation of phospholipase C, activation of MAP kinases, and activation of the small GTP-binding proteins Ras and Rho. Moolenaar, *J. Biol. Chem* 28:1294 (1995). The physiological effects of LPA have not been fully characterized as yet. However, one of the physiological effects that is known is that LPA promotes the growth and invasion of tumor cells. It has been shown that the addition of LPA to ovarian or breast cancer cell lines induces cell proliferation, increases intracellular calcium levels, and activates MAP kinase. Xu et al., *Biochem. J.* 309:933 (1995). In addition, LPA has been shown to induce MM1 tumor cells to invade cultured mesothelial cell monolayers. Imamura et al. *Biochem. Biophys. Res. Comm.* 193:497 (1993).

Like LPA, PA is also a messenger molecule. PA is a key messenger in a common signaling pathway activated by proinflammatory mediators such as interleukin-1β, tumor necrosis factor α, platelet activating factor, and lipid A. Bursten et al., *Am. J. Physiol.* 262:C328 (1992); Bursten et al., *J. Biol. Chem.* 255:20732 (1991); Kester *J. Cell Physiol.* 156:317 (1993). PA has been implicated in mitogenesis of several cell lines [English, Cell Signal 8: 341 (1996)]. PA level has been found to be increased in either ras or fps transformed cell lines compared to the parental Rat2 fibroblast cell line [Martin et al., Oncogene 14: 1571 (1997)].

Activation of Raf-1, an essential component of the MAPK signaling cascade, by extracellular signals is initiated by association with intracellular membranes. Recruitment of Raf-1 to membranes has been reported to be mediated by direct association with phosphatidic acid [Rizzo et al., J Biol Chem 275:23911-8 (2000)]. Thus, LPAAT, as an enzyme that regulate PA content in cells, may play a role in cancer, and may also mediate inflammatory responses to various proinflammatory agents.

SUMMARY OF THE INVENTION

The preferred embodiments of the present invention relate to a compound of the Formula:

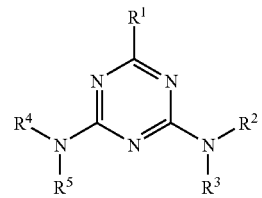

wherein, $R^1$ is halo, hydroxy, alkylmercapto, mercapto, alkoxy, aryloxy or substituted amino;

$R^2$, $R^3$, $R^4$ and $R^5$, each of which may be same or different, are hydrogen, alkyl, substituted alkyl, alkenyl, alkynyl, aryl or substituted aryl; or $R^2$ and $R^3$ or $R^4$ and $R^5$, together with the nitrogen to which they are attached, form a piperidine, piperazine, or a morpholine ring; or pharmaceutically acceptable salts thereof.

The preferred embodiments of the present invention further relate to a method for inhibiting LPAAT-β (lysophosphatidic acid acyltransferase β) comprising contacting LPAAT-β with an effective amount of a compound of the Formula:

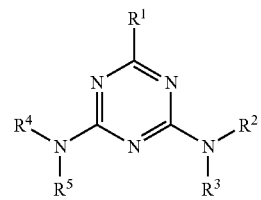

wherein, $R^1$ is halo, hydroxy, alkylmercapto, mercapto, alkoxy, aryloxy or substituted amino;

$R^2$, $R^3$, $R^4$ and $R^5$, each of which may be same or different, are hydrogen, alkyl, substituted alkyl, alkenyl, alkynyl, aryl or substituted aryl; or $R^2$ and $R^3$ or $R^4$ and $R^5$, together with the nitrogen to which they are attached, form a piperidine, piperazine, or a morpholine ring; or pharmaceutically acceptable salts thereof;

thereby inhibiting LPAAT-β.

The preferred embodiments of the present invention further relate to a method of inhibiting cell proliferation comprising contacting a cell with an effective amount of a compound of the Formula:

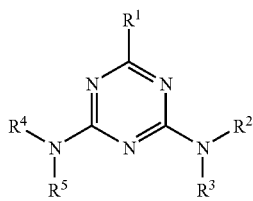

wherein,

R¹ is halo, hydroxy, alkylmercapto, mercapto, alkoxy, aryloxy or substituted amino;

R², R³, R⁴ and R⁵, each of which may be same or different, are hydrogen, alkyl, substituted alkyl, alkenyl, alkynyl, aryl or substituted aryl; or R² and R³ or R⁴ and R⁵, together with the nitrogen to which they are attached, form a piperidine, piperazine, or a morpholine ring; or pharmaceutically acceptable salts thereof;

thereby inhibiting the proliferation of the cell.

The preferred embodiments of the present invention further relate to a method for treating cancer, comprising administering to an animal in need thereof, an effective amount of a compound of the Formula:

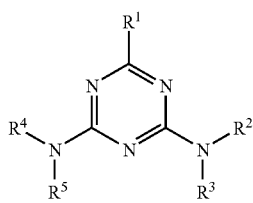

wherein,

R¹ is halo, hydroxy, alkylmercapto, mercapto, alkoxy, aryloxy or substituted amino;

R², R³, R⁴ and R⁵, each of which may be same or different, are hydrogen, alkyl, substituted alkyl, alkenyl, alkynyl, aryl or substituted aryl; or R² and R³ or R⁴ and R⁵, together with the nitrogen to which they are attached, form a piperidine, piperazine, or a morpholine ring; or pharmaceutically acceptable salts thereof;

wherein the cancer is treated.

The preferred embodiments of the present invention further relate to a method for screening a patient for LPAAT-β activity, said method comprising detecting the presence or absence of an increased amount of LPAAT-β RNA, DNA or protein relative to a predetermined control, whereby the presence of said increased amount is indicative of cancer susceptibility in said patient.

The preferred embodiments of the present invention further relate to a method of inhibiting cell proliferation comprising the inhibition of LPAAT-β.

The preferred embodiments of the present invention further relate to a vaccine preparation capable of inducing an anti-tumor immune response comprising a pharmaceutically acceptable carrier and an anti-tumor immune response-inducing effective amount of LPAAT-β protein.

The preferred embodiments of the present invention further relate to a method for screening a patient for LPAAT-β activity, said method comprising detecting the presence or absence of an increased amount of a phospholipid of defined acyl-chain composition relative to a predetermined control, whereby the presence of said increased amount is indicative of cancer susceptibility in said patient.

BRIEF DESCRIPTION OF THE DRAWINGS

FIG. 4E shows the summary of immunohistochemistry results of the various tissue samples stained by MoAb 4B12.

DETAILED DESCRIPTION OF THE PREFERRED EMBODIMENTS

Figure 1:
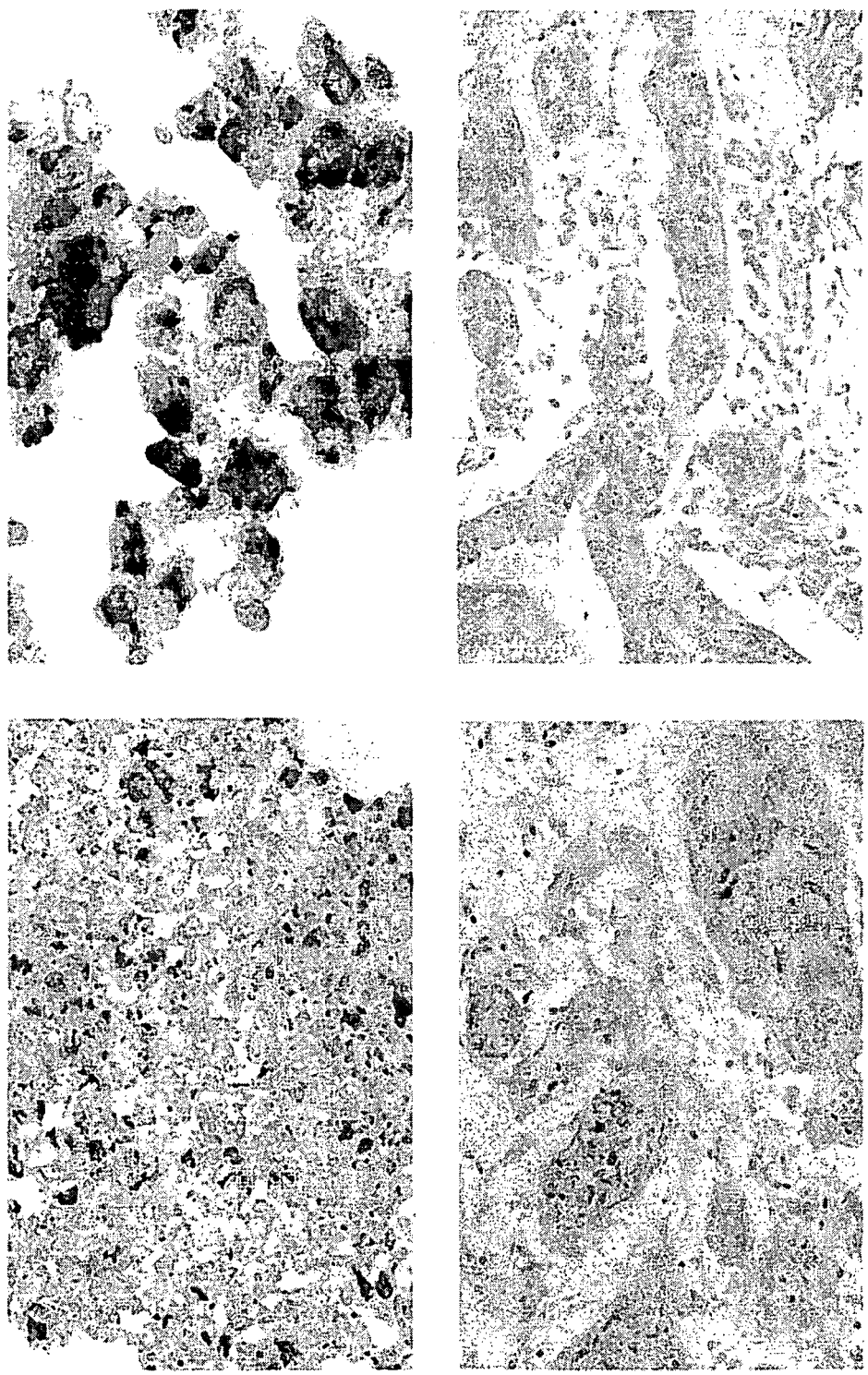
FIG. 1 shows the results on a breast intraductal adenocarcinoma sample where there is moderate increase in LAPPT-β mRNA level in the tumor sample (top two panels).

I. LPAAT-α and LPAAT-β: An Overview.

Northern blot analysis shows that LPAAT-α is expressed in all human tissues tested with the highest expression level found in skeletal muscle (West et al. *DNA Cell Biol.* 16:691 (1997)). The uniformity of LPAAT-α expression has also been found in additional tissues such as prostate, testis, ovary, small intestine, and colon (Stamps et al., *Biochem. J.* 326: 455 (1997)) as well as in mouse tissues (Kume et al., *Biochem. Biophys. Res. Commun.* 237: 663 (1997)). A 2 kb and a 1.3 kb forms, possibly due to alternative utilization of polyadenylation signals at the 3'-UTR, have been found in murine LPAAT-α mRNA (Kume et al., *Biochem. Biophys. Res. Commun* 237: 663 (1997)), whereas only one major human LPAAT-α mRNA of 2 kb in size has been detected by Northern analysis. West et al., *DNA Cell Biol.* 16: 691 (1997); Stamps et al., *Biochem. J.* 326: 455 (1997).

In contrast, LPAAT-β demonstrates a distinct tissue distribution of mRNA expression. West et al., *DNA Cell Biol.* 16: 691 (1997). LPAAT-β is most highly expressed in liver and heart tissues. LPAAT-β is also expressed at moderate levels in pancreas, lung, skeletal muscle, kidney, spleen, and bone marrow; and at low levels in thymus, brain and placenta. This differential pattern of LPAAT-β expression has been confirmed independently (Eberhardt et al., *J. Biol. Chem.* 272: 20299 (1997)) with the only discrepancy being that high level, instead of moderate level, of LPAAT-β has been detected in pancreas, possibly due to slight lot variations in commercial RNA blots (Clontech, Palo Alto, Calif.). In addition, moderate LPAAT-β expression has been found in prostate, testis, ovary, small intestine, and colon with the small intestine containing relatively higher amounts. Eberhardt et al., *J Biol Chem* 272: 20299 (1997). Within various brain sections, high expression has been found in the subthalamic nucleus and spinal cord; and least in the cerebellum, caudate nucleus, corpus callosum, and hippocampus. LPAAT-β can also be detected in myeloid cell lines THP-1, HL-60, and U937 with the mRNA levels remaining the same with or without phorbal-ester treatment. The size difference between human LPAAT-α and LPAAT-β mRNA is consistent with the sequence data, in which LPAAT-α has a longer 3'-UTR. The differential tissue expression pattern LPAAT-α and LPAAT-β mRNA would suggest these two genes are regulated differently and are likely to have independent functions. Therefore, a desirable feature in compounds that inhibit LPAAT activity is that they are specific in inhibiting one isoform of the enzyme over the other (i.e., LPAAT-β over LPAAT-α).

II. LPAAT-β and Cancer.

PA has been implicated in mitogenesis of several cell lines. English, *Cell Signal* 8: 341 (1996). PA level has been found to be increased in either ras or fps transformed cell lines compared to the parental Rat2 fibroblast cell line (Martin et al., *Oncogene* 14: 1571 (1997). To test whether LPAAT expression may be enhanced in certain tumor cells, the expression of LPAAT-α and LPAAT-β mRNA in human tumor panel blots (Invitrogen, Carlsbab, Calif.) that contained tumor RNAs, isolated from various malignant tissues and RNAs from the normal tissues in the surgical margins, were examined. Leung et al., *DNA Cell Biol.* 17: 377 (1998). The same blots were also reprobed using cDNAs encoding phosphatidic acid phosphatase isoform PAP2-α; an enzyme that degrades, rather than generates, PA. Of a total of eight different tissues examined, LPAAT-β mRNA was found to be elevated in three tumors tissues (uterus, fallopian tube, and ovary), as compared to its expression in the corresponding normal tissues. However, no significant difference was found in LPAAT-α mRNA level between the various tumor tissues and the normal adjacent tissues. In two of the tumor tissues (fallopian tube and ovary) where LPAAT-α mRNA was elevated, PAP2-α mRNA expression was found to be suppressed, as it was also in tumors of the colon, rectum, and breast.

Since the finding of differential expression of LPAAT-β mRNA in certain tumor versus normal tissues is based on Northern analysis of a single specimen from a given tissue, more studies will be needed to determine whether the relative elevation of LPAAT-β expression in selected tumor tissues can be applied and extended to similar tissues derived from a larger number of donors. Leung et al., *DNA Cell Biol.* 17: 377 (1998). Accordingly, in situ hybridization was used to compare LPAAT-β mRNA levels in breast, ovary, and prostate tumor samples obtained from multiple independent donors (LifeSpan Biosciences, Seattle, Wash.). Specifically, the coding region of human LPAAT-β was amplified by PCR from the plasmid pCE9. LPAAT-β with primers 5'-GCATGAATTC AAAGGCCTAC GTCGACATGG AGCTGTGGCC GTG-3' (SEQ ID NO:1) and 5'-GTCGACTCTA GACTACTGGG CCGGCTGCAC-3' (SEQ ID NO:2). The resultant 870 bp PCR product was then cut with EcoR I and XbaI for insertion in between the EcoR I and XbaI sites of the in vitro transcription vector pDP18-T7/T3 (Ambion, Austin, Tex.) to generate the plasmid pDP__1ptB. Serial tissue sections from paraffin archival samples were hybridized with digoxigenin labeled riboprobes transcribed from either a T3 (sense) or T7 (antisense) transcription initiation site present in the plasmid pDP__1ptB linearized with either EcoR I (antisense) or Xba I (sense). The tissue sections from paraffin blocks were digested with proteinase K (20 µg/ml) for 4 minutes, then hybridized with the antisense probe (1 µg/ml) at 60° C. for 22 hours and subsequently washed with 2×SSC and 0.1×SSC at 50° C. The hybridization signals were detected with NBT/BCIP substrates using three cycles of an alkaline phosphatase TSA amplification system (NEN Life Sciences, Boston, Mass.). The specimens were then counterstained with methyl green. The signal was developed within 30 minutes at room temperature. The slides were then imaged using a digital camera mounted onto a microscope.

Figure 2:
FIG. 2 shows the results on a breast intraductal adenocarcinoma sample where there is a large increase in LPAAT-β mRNA level in the tumor sample.
Figure 2:
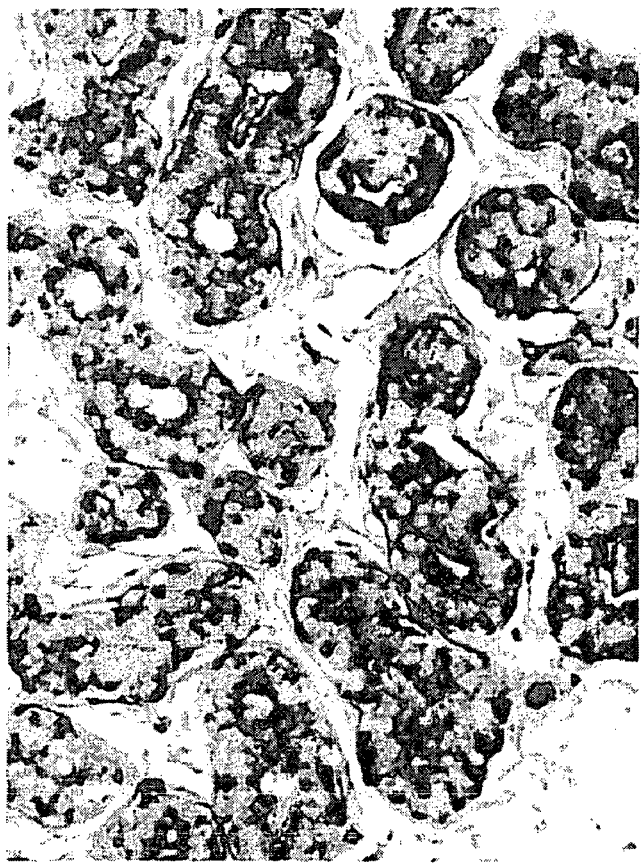
Figure 3:
FIG. 3 shows three examples of ovarian cancer where the LPAAT-β mRNA levels are elevated and one example with undetectable level of LPAAT-β mRNA (lower right panel).
Figure 3:
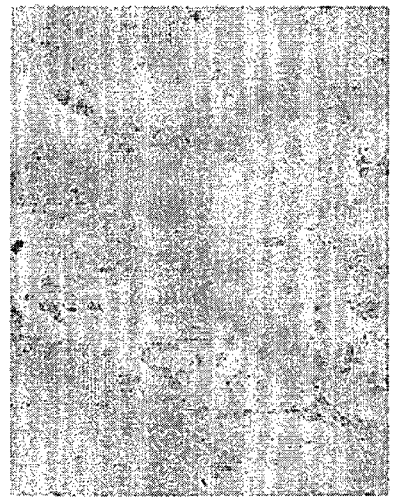
Figure 3:
Figure 3:
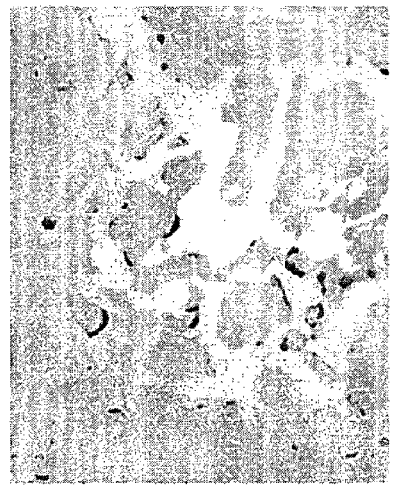
Figure 4A:
FIG. 4A shows the results on a prostate adenocarcinoma sample where there is moderate increase in LPAAT-β mRNA level in the tumor sample.
Figure 4A:
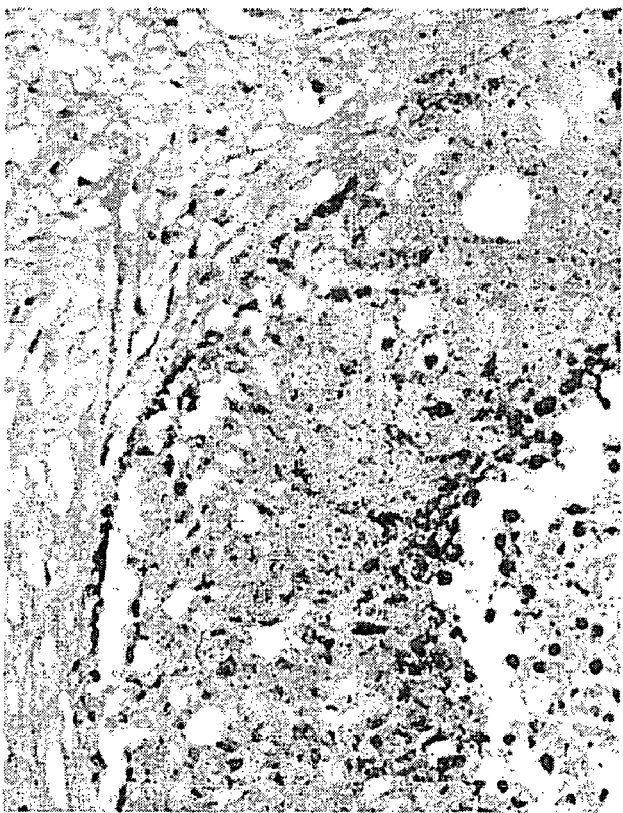

Breast and ovary tissues were chosen for further in situ hybridization study, as initial Northern analysis showed elevation of LPAAT-β mRNA levels in tumors derived from the female reproductive tract. Prostate tissue was chosen, as it responds to steroid hormones and contains ductal structures in a manner similar to breast and ovary tissues. Using an anti-sense cDNA probe, it was demonstrated that expression of the β isoform of this enzyme (LPAAT-β) was augmented in human tumor tissue in 10/11 ovarian, 14/20 breast, and 7/16 prostate biopsies as compared to normal adjacent tissues. FIG. 1 shows an example of the results on a breast intraductal adenocarcinoma sample where there is moderate increase in LPAAT-β mRNA level in the tumor samples (top 2 panels) as evidenced by more dark-purple to brown spots compared to adjacent hyperplasia (bottom-left panel) and normal tissue (bottom-right panel). The slight increase in LPAAT-β mRNA staining in the hyperplasia sample (bottom-left panel) versus the normal sample (bottom-right panel) suggests that elevation occurs at an early stage of oncogenesis. FIG. 2 shows an example of the results on another breast intraductal adenocarcinoma sample where there is large increase in LPAAT-β mRNA level in the tumor sample (left panel) as evidenced by more dark-purple spots versus the adjacent normal tissue (right panel). FIG. 3 shows three examples of ovarian cancer samples where the LPAAT-β mRNA levels are elevated and one example with undetectable level of LPAAT-β mRNA (lower right panel). FIG. 4A shows an example of the results on a prostate adenocarcinoma sample where there is moderate increase in LPAAT-β MRNA level in the tumor samples (left panel) as evidenced by more dark-purple spots versus the adjacent normal tissue (right panel). In no cases have elevated levels of LPAAT-β mRNA expression been found in the adjacent normal region from the same donor even in those cases of breast, ovarian, or prostate tumor where LPAAT-β mRNA levels happen to be low or undetectable. The augmented expression of LPAAT-β in a high percentage of tumor samples from breast (70%), ovary (91%), and prostate tissues (44%) would suggest that LPAAT-β overexpression may be a contributing factor for the development of these tumors.

Figure 4B:
FIG. 4B shows the results on immunohistochemical staining of ovarian tissue with MoAb 4B12.
Figure 4B:
Figure 4B:
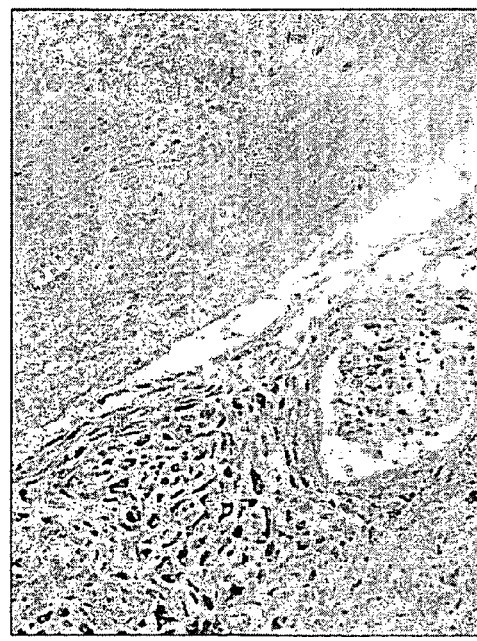
Figure 4C:
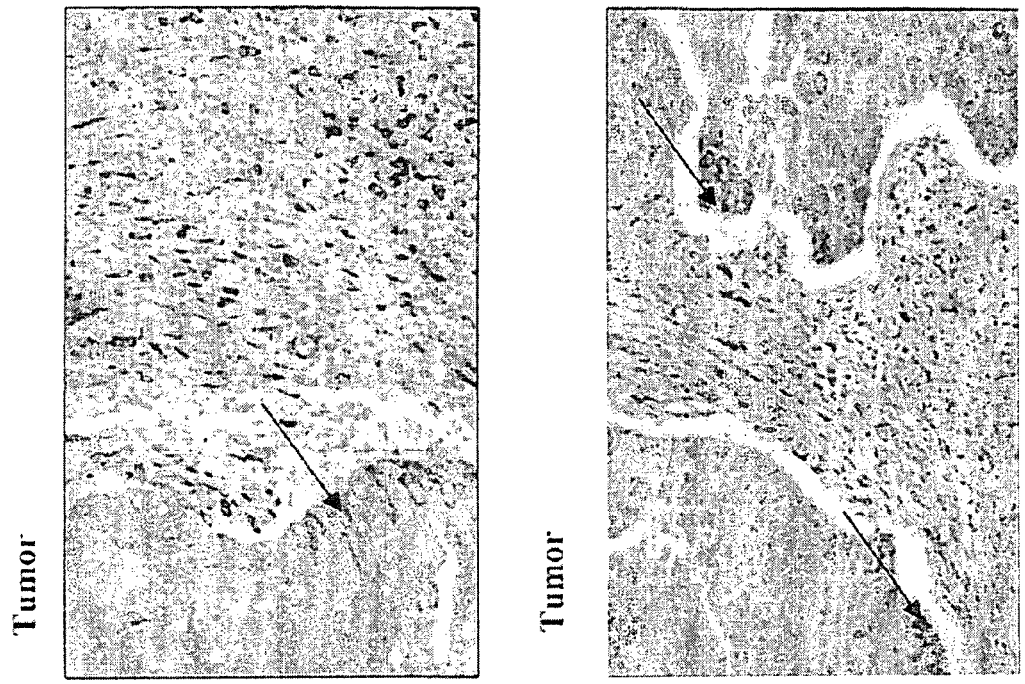
FIG. 4C shows the results on immunohistochemical staining of cervical tissue with MoAb 4B12.
Figure 4C:
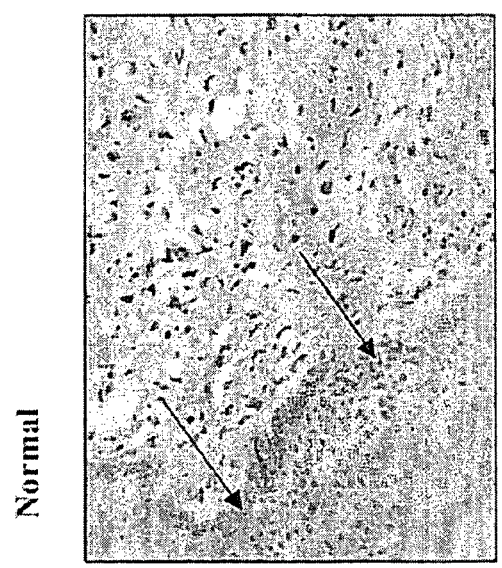
Figure 4D:
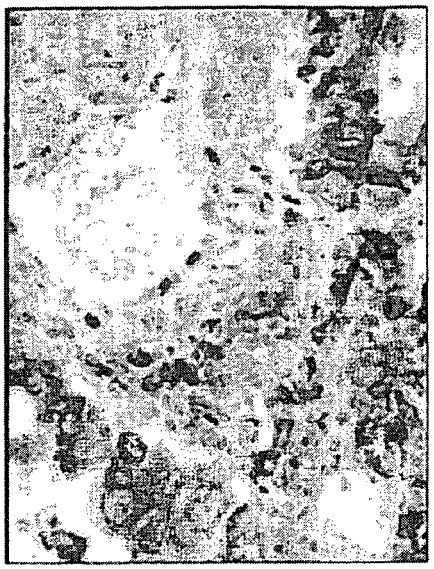
FIG. 4D shows the results on immunohistochemical staining of lung tissue with MoAb 4B12.
Figure 4D:
Figure 4D:

To determine if increased transcription of LPAAT-β mRNA in selected tumor tissues can be extended to increased LPAAT-β protein expression in a wider range of tissues, a monoclonal antibody specific for human LPAAT-β protein (MoAb 4B12) was generated based on the petide sequence, DLGERMVRENLKVW, derived from amino acids 155-168 of LPAAT-β protein (BAbCO, Berkeley, Calif.). FIG. 4B shows an example of the results on immunohistochemical staining (PhenoPath, Seattle, Wash.) with MoAb 4B12 at 1:4000 dilution of ovarian tissue where there is substantial increase in LPAAT-β protein expression in the tumor samples (right panels) as evidenced by more intense brown stainings versus the normal tissue (left panel). FIG. 4C shows an example of the results on immunohistochemical staining (PhenoPath, Seattle, Wash.) with MoAb 4B12 at 1:4000 dilution of cervical tissue where there is substantial increase in LPAAT-β protein expression in the tumor samples (right panels) as evidenced by more intense brown stainings versus the normal tissue (left panel). There is also more staining in the surrounding stromal cells (indicated by arrows) in the tumor tissue vs the normal tissue, suggesting that the tumor may also induce LPAAT-β protein expression in the surrounding cells. FIG. 4D shows another example of the results on immunohistochemical staining (PhenoPath, Seattle, Wash.) with MoAb 4B12 at 1:4000 dilution of lung tissue where there is extensive increase in LPAAT-β protein expression in the tumor samples (right panels) as evidenced by more intense brown stainings versus the normal tissue (left panel). FIG. 4E shows the summary of immnohistochemistry (IHC) results of the various tissue samples stained by MoAb 4B12. The augmented expression of LPAAT-β in a high percentage of tumor samples again suggest that LPAAT-β overexpression may be a contributing factor for the development of these tumors and that LPAAT-β may be a useful target for the development of anti-cancer compounds.

The aforementioned antibody may also be used for diagnostic and prognostic purposes when a tumor is present both on biopsies and in serum or plasma. For example, ELISA may be performed on serum to detect lung or ovarian cancer. It should be mentioned that currently there are no useful early diagnostics for these types of cancers.

The overexpression of LPAAT-β in selected tumor tissues would also suggest the LPAAT-β protein may constitute a useful antigen for the development of tumor vaccines against those tumors where LPAAT-β is overexpressed. Fong et al., *Annu. Rev. Immunol.* 18: 245 (2000); Schreurs, et al., *Crit. Rev. Oncol.* 11: 1 (2000). One such approach may use autologous dendritic cells, a type of potent antigen-presenting cells, to present LPAAT-β as a tumor-associated antigens for the generation of tumor-specific immunity through the MHC class I and II processing pathways. Administration of dendritic cells loaded ex vivo with LPAAT-β as a therapeutic vaccine to patients with tumors with augmented LPAAT-β expression may induce T cell-mediated tumor destruction.

Figure 5A:
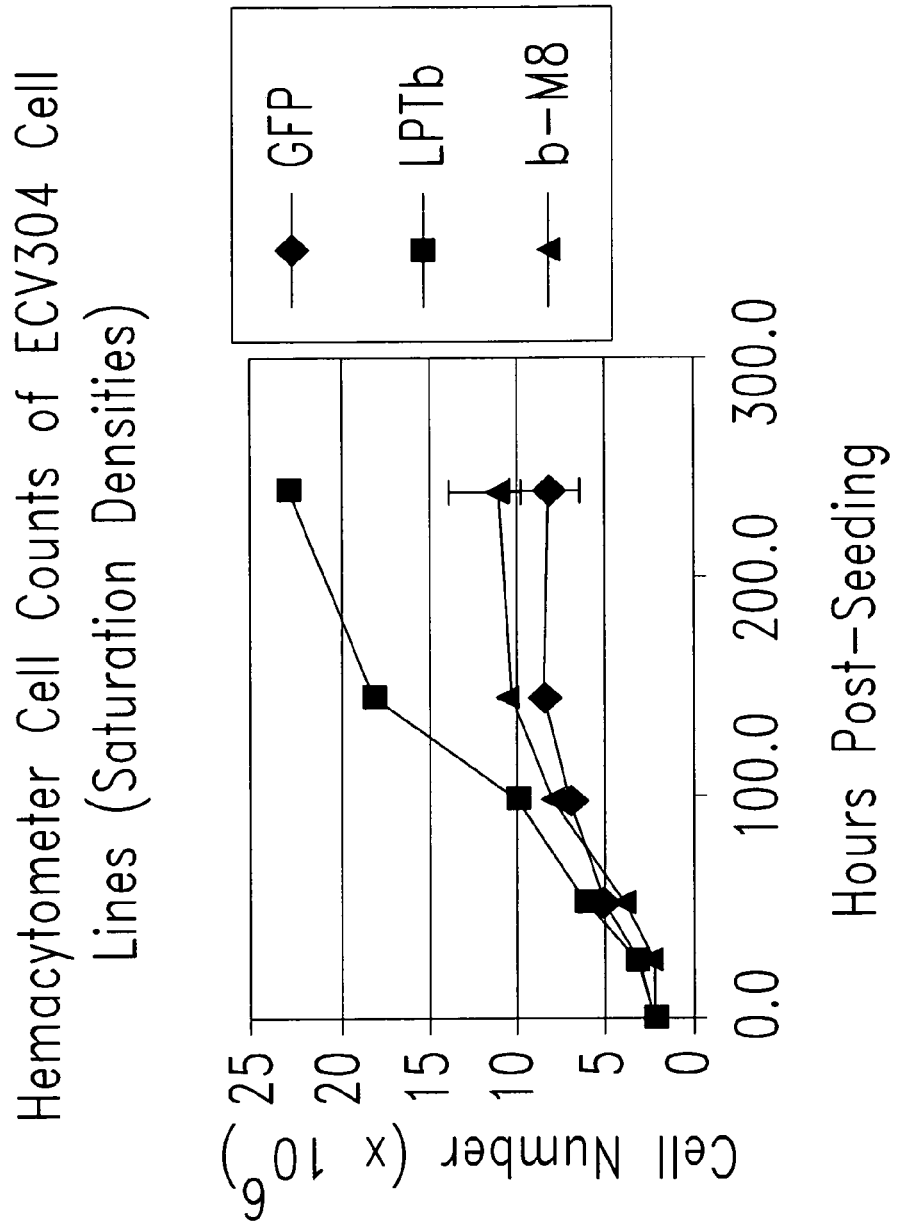
FIG. 5A shows hemacytometer cell counts of ECV304 cell lines.

To assess whether LPAAT-β overexpression in cells would lead to certain phenotypic changes that are commonly observed in transformed cells, the growth and adherence characteristics of ECV304 cells (American Type Culture Collection, Richmond, Va.) expressing LPAAT-β (LPTb), expressing a catalytically inactive form of LPAAT-β (b-M8) whereby the arginine at position 175 was changed to alanine using the GeneEditor™ in vitro site-directed mutagenesis system (Promega, Madison, Wis.), or expressing green fluorescent protein (GFP) as a control were compared. The aforementioned cells that express GFP may be considered to be a non-limiting example of a "predetermined control," according to the preferred embodiments of the present invention. That is, such cells may be used to gauge whether a cell is over- or under-expressing LPAAT-β DNA, RNA or protein. FIG. 5A shows the growth curve of these three cell lines. Each cell line was seeded at 200,000 cells per 60 mm plate. The cell numbers at various times after seeding were determined by counting with a hemacytometer. The growth rate of the three cell lines were similar until they reached confluence at 100 hours after plating. After confluence, the LPTb cells were able to continue to proliferate, while the b-M8 and GFP cells' growth started to level off. This demonstrated that ECV304 cells overexpressing LPAAT-β could continue to grow and could form a plurality of layers after they had formed a confluent monolayer of cells. The proliferation of the cells with the inactive mutant or the control cells slowed down after confluence. The loss of contact inhibition and the propensity for growth to an unusually high cell density are changes commonly observed in tumorigenesis. The fact that the inactive LPAAT-β mutant (b-M8) expressing cells, like the vector control cells, are constrained by density-dependent inhibition of cell division strongly suggests that the capacity to overcome contact inhibition may be due to increases in LPAAT-β enzymatic activity. The development of compounds that inhibit LPAAT-β enzymatic activity may reverse the growth pattern and hence tumorigenesis in cells with abnormally high level of LPAAT-β expression.

To determine if the observation from LPAAT-β expressing ECV304 cells can be extended to other cell types and to animal models of tumorigenesis, LPAAT-β cDNA was inserted into a retroviral expression vector, pLOXSN, for the generation of recombinant viral stocks in a packaging cell line, PT67 (Clontech, Palo Alto, Calif.), for transduction into various cell lines. The vector pLOXSN was derived from pLXSN with insertion of a 19 bp oligonucleotide coding for the locus of recombination (lox) signal sequence as well as a ClaI recognition site into the NheI site within the 3'-LTR region of pLXSN. Miller and Rosman *BioTechniques* 7: 980 (1989); Hoess. and Abremski, *Nucleic Acid and Mol. Biol.* 4: 99 (1990). This lox sequence will be duplicated within the 5'-LTR region during viral replication. Hence the sequence in between the two lox sites located within the 5'- and the 3'-LTR can be excised if required in the presence of the enzyme cre recombinase supplied in trans from a separate retroviral vector with a different selectable marker.

Figure 5B:
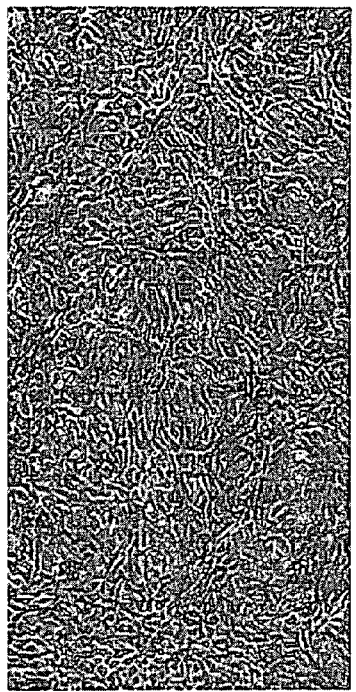
FIG. 5B shows examples of cell morphology of NIH/3T3 cells after exposure to specified agents.
Figure 5B:
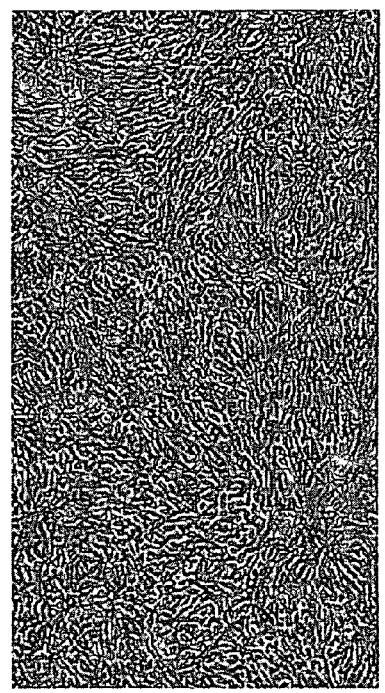
Figure 5B:
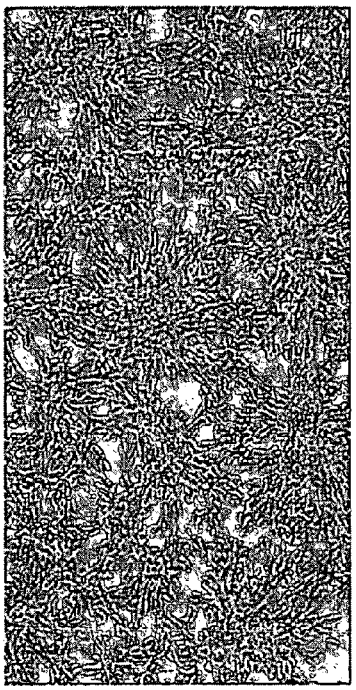
Figure 5B:

Over-expression of the normal cellular LPAAT-β cDNA in NIH/3T3 cells was associated with transformation in 3 out of 9 transduced populations. As is the case with normal cellular proto-oncogenes, over-expression of LPAAT-β is not sufficient, but may contribute to transformation along with other, spontaneous events. FIG. 5B shows examples of cell morphology of NIH/3T3 cells: a bulk population transfected with a plasmid overexpressing the Ki-ras oncogene (top left panel), a selected clone transduced with a retroviral vector overexpressing LPAAT-β (Hc2; lower left panel) and cells with the LPAAT-β cDNA excised using the lox-cre recombination in the lower left and normal, untransduced cells (top right panel). Sauer, *Methods* 14: 381 (1998). The control untransduced cells exhibited normal fibroblast morphology and grew as a contact-inhibited, adherent monolayer (top right panel). In contrast, both the Ki-ras and LPAAT-β overexpressing cells were more elongated and spiked, were not contact-inhibited and formed foci typical of transformation of these immortalized fibroblasts. After removal LPAAT-β transgene by lox-cre recombination from the Hc2 clone (bottom right panel), this transformed morphology was lost, suggesting that LPAAT-β overexpression is a contributing factor to this transformation phenotype rather than being the result entirely of spontaneous events during in vitro passage.

Figure 5C:
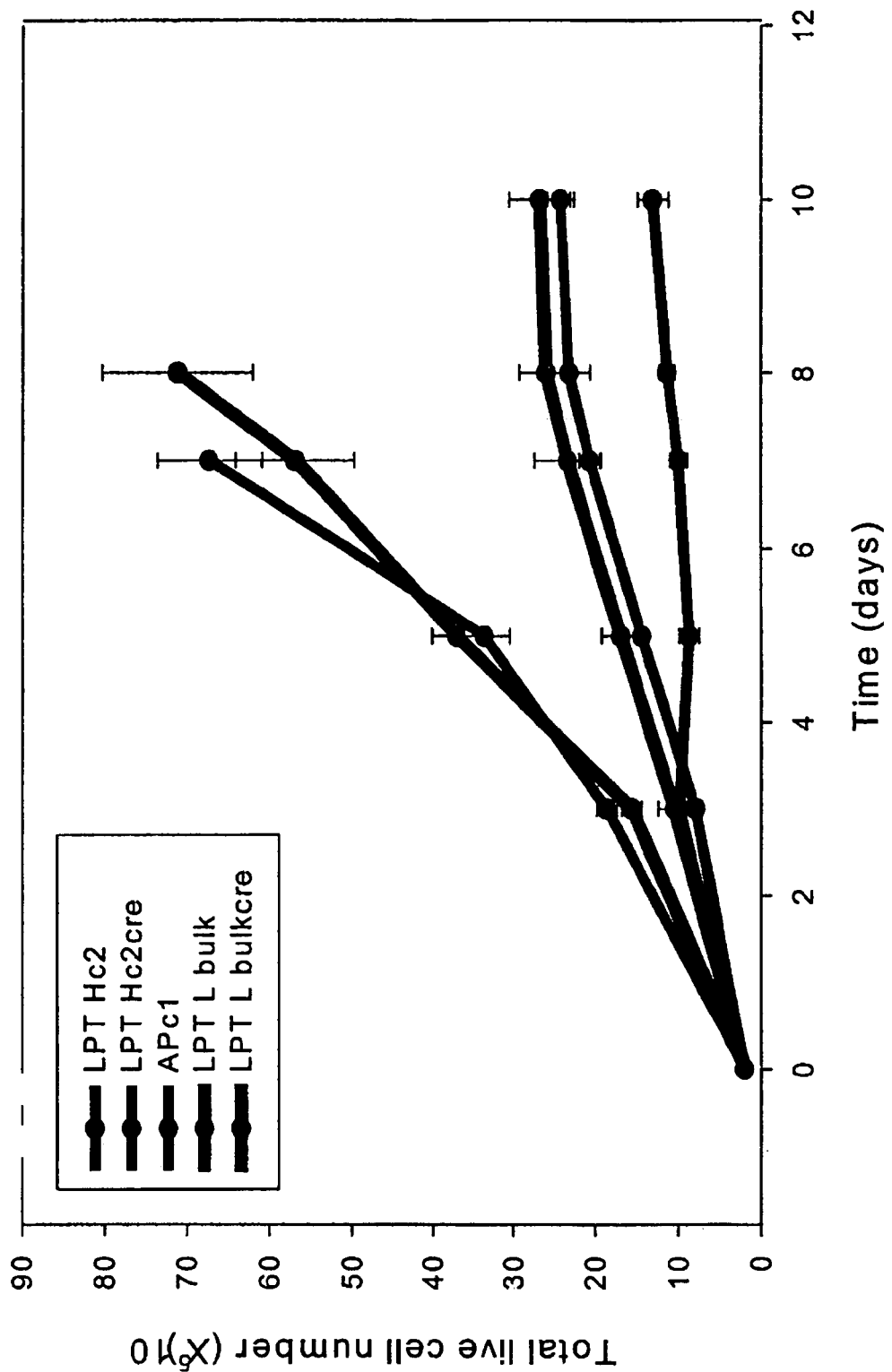
FIG. 5C shows the growth profiles of transduced populations of NIH/3T3 cells.

Another common parameter of cancer cells is a reduced requirement for elements present in serum. FIG. 5C compares the growth profiles of transduced populations of NIH/3T3 cells in low (2%) serum. Two independent populations (LPT Hc2, LPT L bulk) overexpressing LPAAT-β have an increased ability to proliferate compared to a control vector clone expressing alkaline phosphatase (APc1) and those corresponding populations with deletion of the LPAAT-β transgene by lox-cre recombination (LPT Hc2cre, LPT L bulkcre), suggesting that LPAAT-β overexpression is a contributing factor to this transformed phenotype of proliferation with a reduced requirement for growth factors.

Figure 5D:
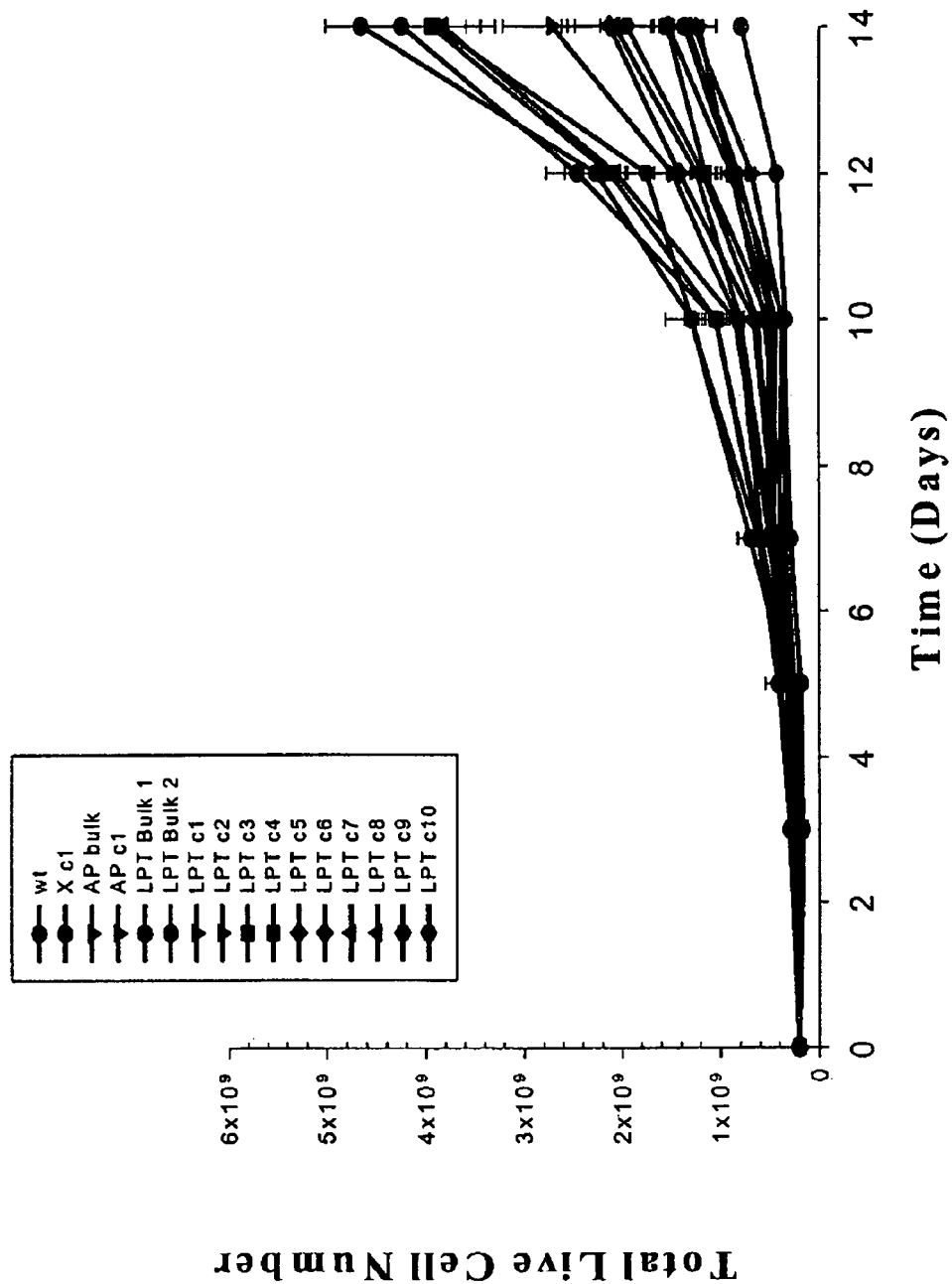
FIG. 5D shows the growth profiles of transduced populations of LNCaP cells.

Similarly, out of a total of 12 populations of human prostate LNCaP cells (American Type Culture Collection, Manassas, Va.) transduced with LPAAT-β expressing vector, most of them show augmented proliferation in low serum when compared to control cells (FIG. 5D).

Figure 5E:
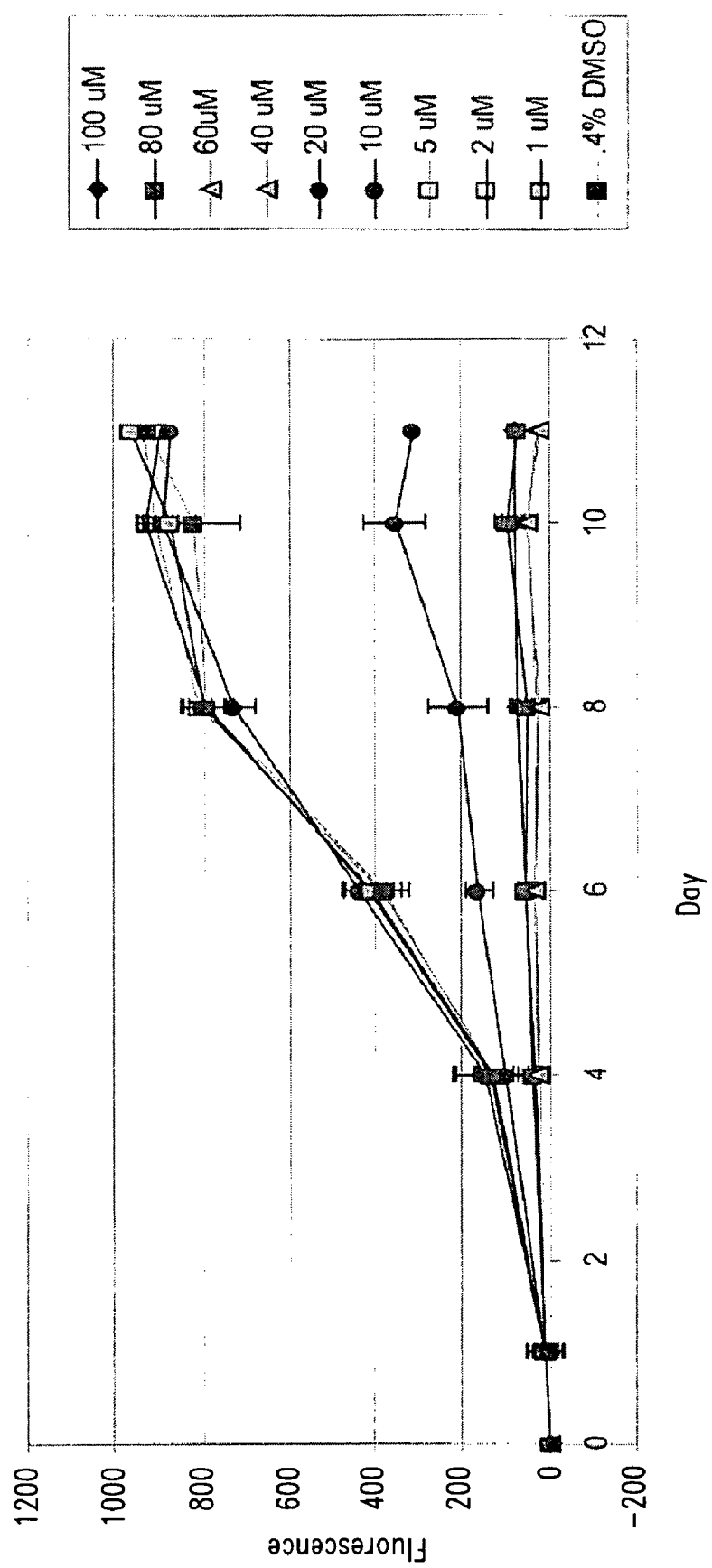
FIG. 5E shows the effect of 6-chloro-N,N'-diphenyl-[1,3,5]triazine-2,4-diamine on the proliferation of MCF-7 cells.

To determine whether administration of LPAAT-β inhibitor would have any effect on cell proliferation in tissue culture, proliferation of human breast tumor MCF-7 cells in microplates were measured by CyQUANT analysis using a green-fluorescent nucleic acid stain optimized to produce a linear detection range from 50 to 50,000 cells in 200 μl volume (Molecular Probes, Eugene, Oreg.) in the presence of various concentrations of a LPAAT-β inhibitor. FIG. 5E shows the triazine compound shows 6-chloro-N,N'-diphenyl-[1,3,5]triazine-2,4-diamine at >20 μM is effective in blocking the proliferation of MCF-7 cells.

Figure 6A:
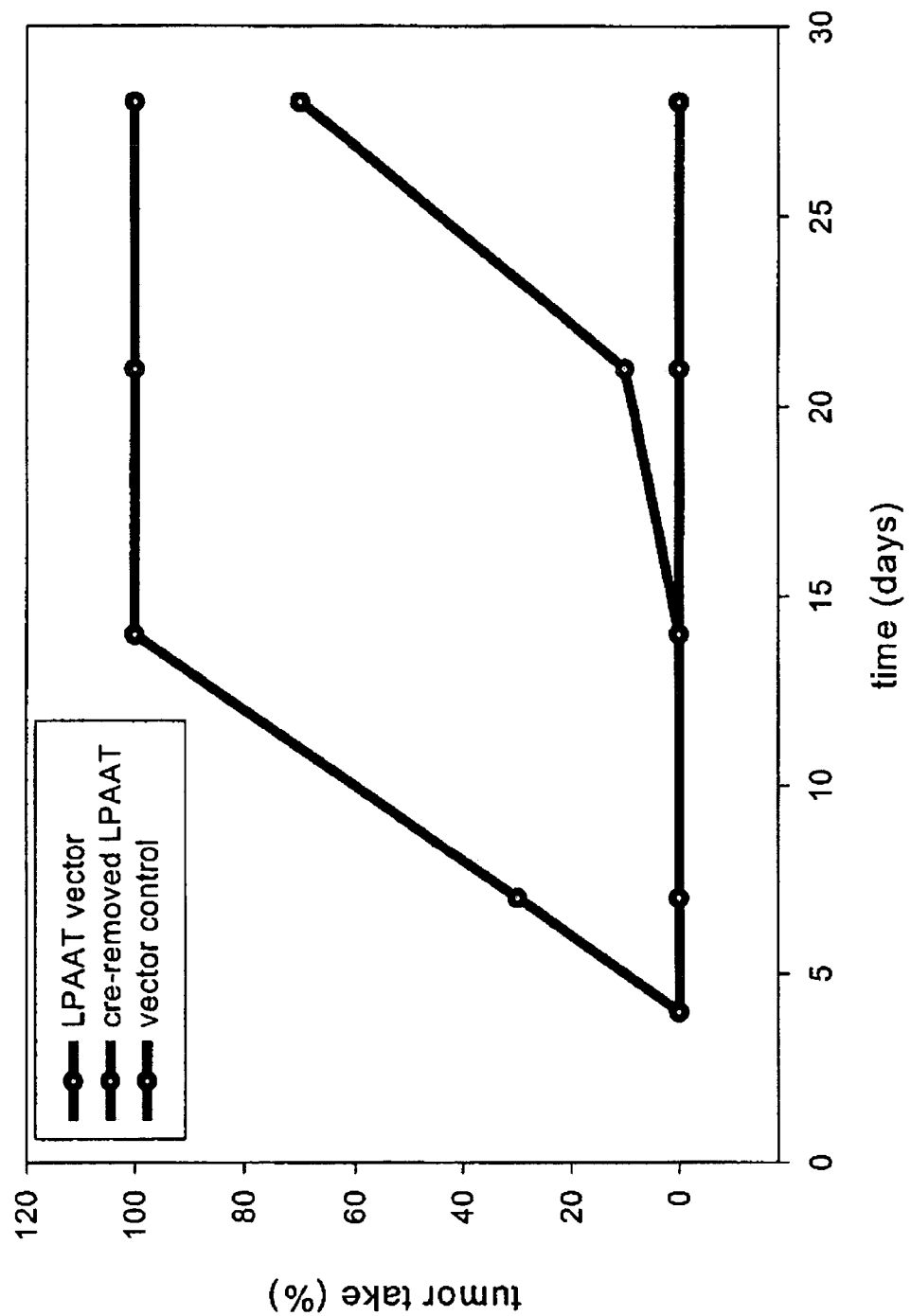
FIG. 6A shows detection of tumor formation from LPAAT-β overexpressing cells.

To determine if LPAAT-β overexpression would contribute to tumorigenesis in mice, $2 \times 10^6$ NIH3T3 cells overexpressing LPAAT-β (LPAAT vector) and control cells were injected subcutaneously into nude mice. FIG. 6A shows tumor could be detected after 14 days from the LPAAT-β overexpressing cells, while no tumor formation was detected in vector control cells after 28 days. The cells with the transgene removed by lox-cre recombination showed delay of tumor formation compared to LPAAT-β overexpressing cells by ~7 days. Recovery and analysis of the lox-cre cells from mice showed that there had been in vivo selection of a small sub-population that had not been recombined to remove the LPAAT-β transgene. This analysis demonstrated that the only cells to form tumors retained the original LPAAT vector and indeed had a high level of LPAAT activity as well as G418 resistance (the neo gene is also removed along with LPAAT-β during the cre-lox procedure). These data show LPAAT-β overexpression is a contributing factor for tumorigenesis in vivo.

Figure 6B:
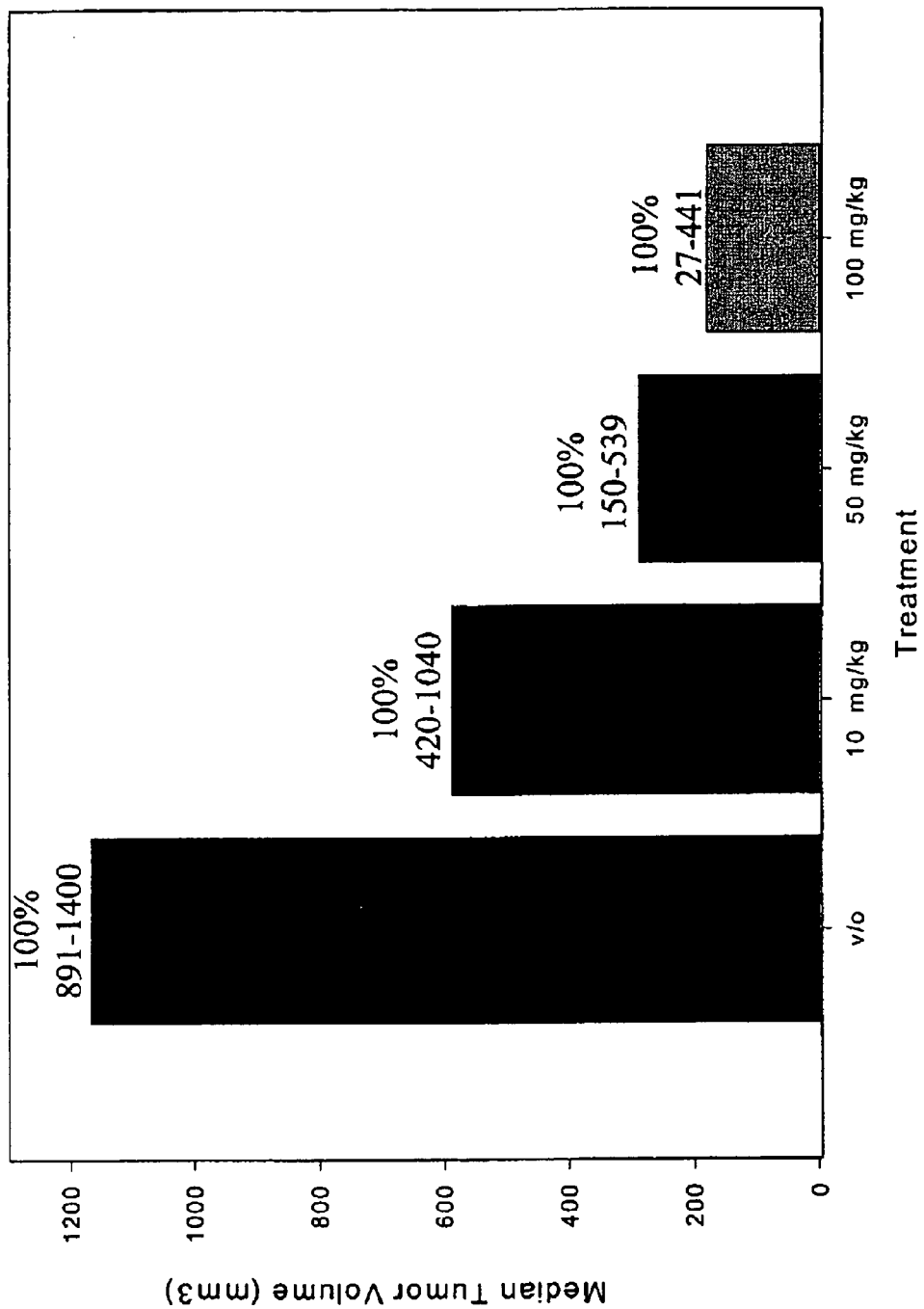
FIG. 6B shows the effect of 6-chloro-N,N'-diphenyl-[1,3,5]triazine-2,4-diamine on the volume of tumors in mice.

To determine whether administration of LPAAT-β inhibitor would have any effect on tumor growth in mice, $5 \times 10^5$ NIH/3T3 cells overexpressing the oncogene Ki-ras were injected subcutaneously into nude mice. An LPAAT-β inhibitor 6-chloro-N,N'-diphenyl-[1,3,5]triazine-2,4-diamine, at concentrations that range from 10 mg/Kg to 100 mg/Kg of mouse body weight was injected intra-peritoneally on day 1, 2, 3 and 4 after injection of tumor cells. The size of tumors was then measured on day 8. FIG. 6B shows the volume of the tumors in mice is decreased as the concentration of the LPAAT-β inhibitor increases, suggesting that administration of this LPAAT-β inhibitor is efficacious in slowing down tumor growth in vivo.

Figure 6C:
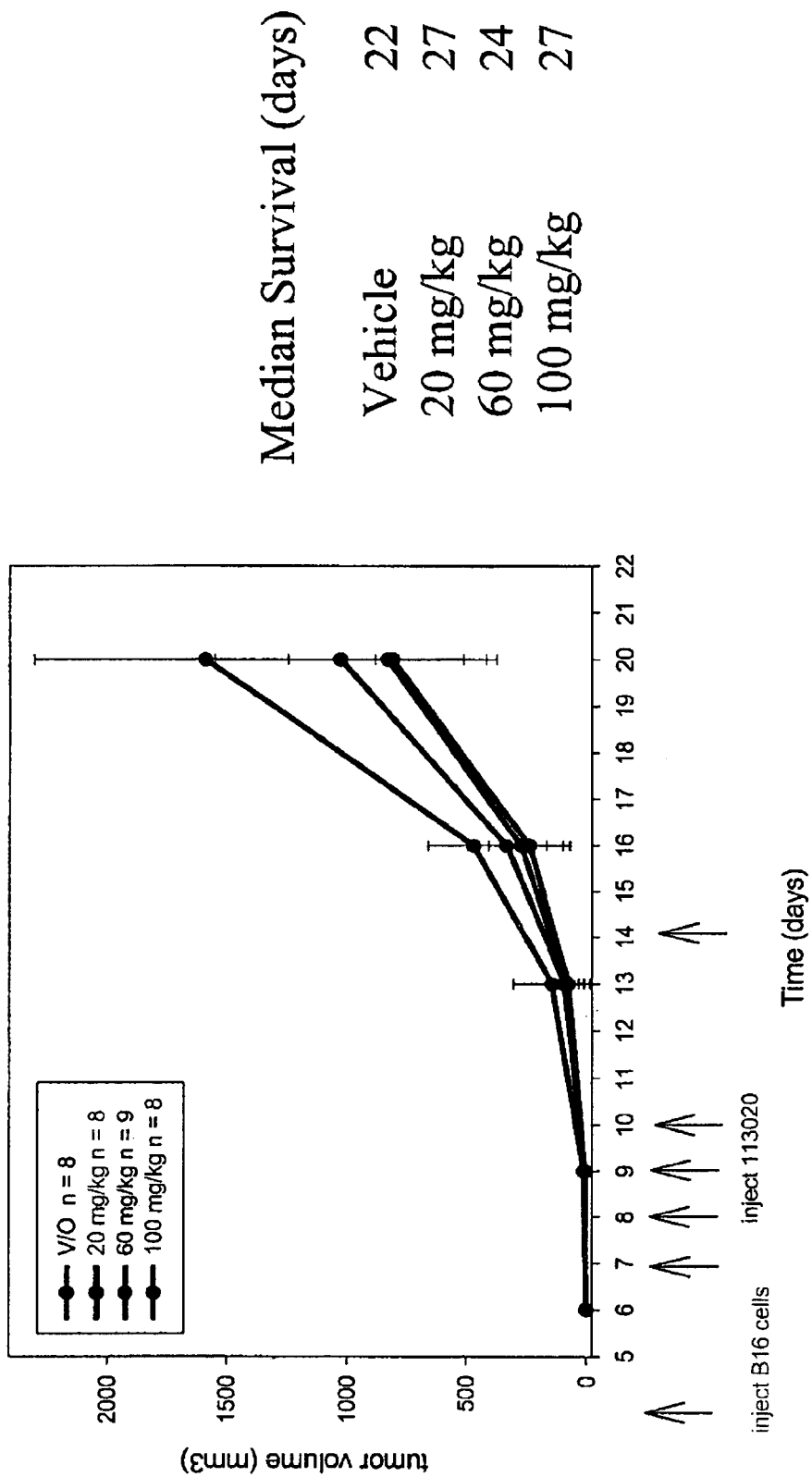
FIG. 6C shows the effect of 6-chloro-N,N'-diphenyl-[1,3,5]triazine-2,4-diamine on the growth of B16 melanoma cells.
Figure 6D:
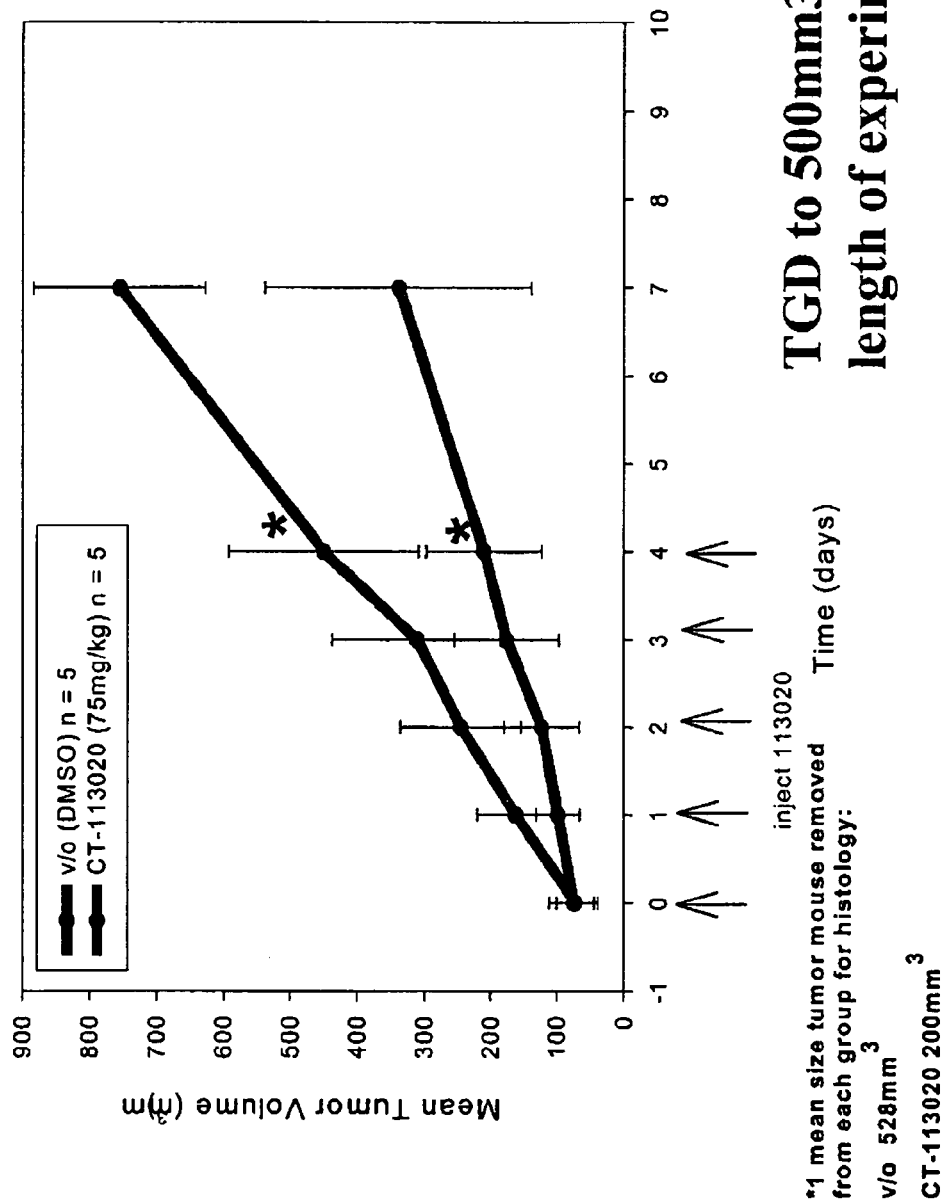
FIG. 6D shows the effect of 6-chloro-N,N'-diphenyl-[1,3,5]triazine-2,4-diamine on the growth of Lewis Lung tumor cells.
Figure 6E:
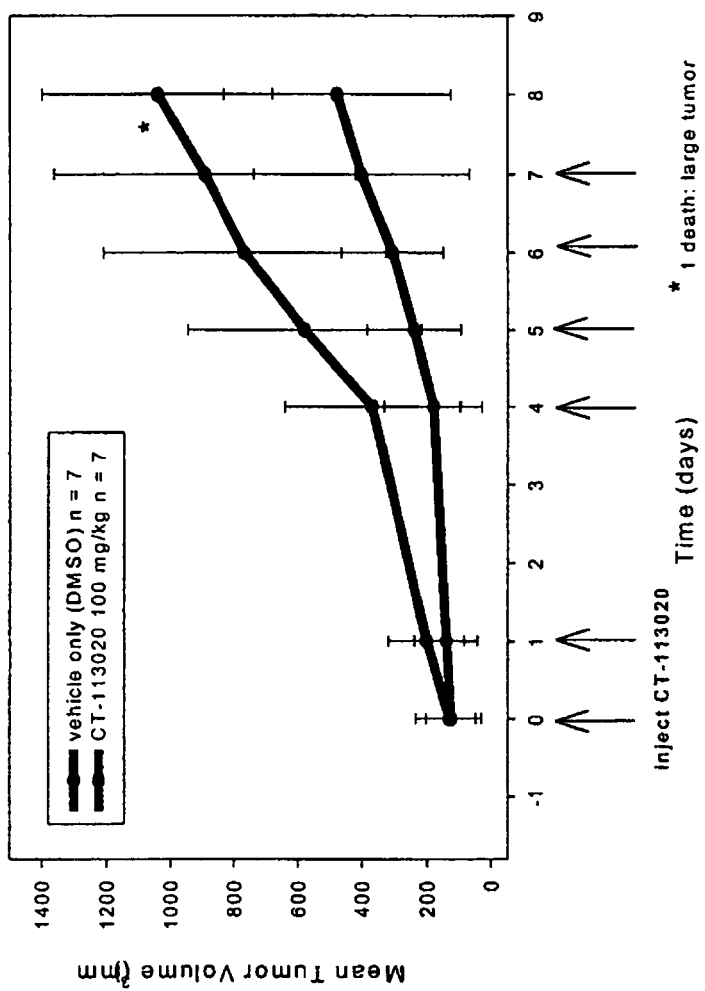
FIG. 6E shows the effect of 6-chloro-N,N'-diphenyl-[1,3,5]triazine-2,4-diamine on the growth of DU145 prostate tumor cells.

In addition to slowing down tumor growth of NIH3T3/Ki-ras cells in nude mice, 6-chloro-N,N'-diphenyl-[1,3,5]triazine-2,4-diamine has also been found to decrease the growth of B16 melanoma cells (FIG. 6C) and Lewis Lung tumor cells (FIG. 6D) in syngeneic mice as well as the growth of human DU145 prostate tumor cells in nude mice in a xenograft study (FIG. 6E).

Analysis and characterization of phospholipids and other complex lipids represent another strategy to measure effects of small molecule inhibitors on phospholipid metabolizing enzymes involved in tumor progression, including but not limited to, LPAAT-β. Measurements of phospholipids and other complex lipids may be derived from cell lines cultured in vitro, from tissue or plasma in vivo (e.g., murine or other animal studies), or from human subjects (e.g., phlebotomy or biopsy). Phospholipids, which are the primary constituents of a cellular bilayer, contain a universal phosphoric acid residue connected to a glycerol backbone. Phospholipid classes are defined by the chemical identity of the "head group" on the phosphoric acid moiety. However, each phospholipid class is often a complex mixture of discrete molecular species due to the fact that the glycerol backbone has two substituents residing at the Sn1 and Sn2 position of attachment. The substituents are acyl chains and typically consist of long chain fatty acids but may also include a long chain ether, acetyl, or hydroxyl group. Chemical measurements of phospholipids can involve a variety of analytical methods including, but not limited to, HPLC-MS (High Performance Liquid Chromatography-Mass Spectrometry), HPLC-MS/MS (High Performance Liquid Chromatography-Tandem Mass Spectrometry), one or two dimensional TLC (Thin Layer Chromatography), and radiometry. While all the stated methods can be used to quantitate bulk mass changes in a particular phospholipid class of interest, mass spectrometry offers the unique ability to measure all molecular species within a phospholipid class in a single measurement with a high degree of precision.

The above approach is demonstrated by performing HPLC-MS analyses of phospholipid extracts from murine NIH/3T3 immortalized fibroblasts, both normal wild type, βHc2 cells (i.e., overexpressing LPAAT-β, and Hc2cre cells (i.e., LPAAT-β gene removed by site-specific recombination). Analysis of phosphatidylinositol in these cell populations clearly indicate a combined effect of LPAAT-β overexpression and cellular transformation for the Hc2 population over that of the normal wild type. This effect is characterized by an increase in unsaturated (i.e., palmitate and stearate) and monounsaturated (i.e., oleate) fatty acyl chains indicated by an increased molecular abundance of ions at m/z 807, 833, 835, 861, and 863 which correspond most likely to phosphatidylinositol species with acyl chains designated as 16:0-16:1, 16:1-18:1 (and/or 16:0-18:2), 16:0-18:1, 18:1-18:1 (and/or 18:0-18:2), and 18:0-18:1, respectively. While multiple molecular species may reside at the same nominal mass, these species can be differentiated by tandem (MS/MS) mass spectrometry methods. Additionally, note that actual determination of positional location (i.e., Sn1 versus Sn2) requires other analytical methods and only the most prevalent configuration is listed here. In addition to the increase in unsaturated and monounsaturated acyl chains in the LPAAT-β overexpressing population (βHc2), there is also a corresponding decrease in polyunsaturated (i.e., arachidonate) fatty acyl chains at m/z 857 (16:0-20:4) and m/z 885 (18:0-20:4). Removal of the LPAAT-β transgene results in phosphatidylinositol distributions similar to that of the normal wild type 3T3 cells.

In summary, endogenous LPAAT-β expression is detected at high levels by both in situ hybridization and immunohistochemistry in particular tumor tissues and often in surrounding stroma and is associated with tumor progression. LPAAT-β overexpression appears to contribute reversibly to transformation and tumorigenesis of immortalized rodent cells and may also contribute to increased transformation of weakly tumorigenic human cell lines. Compounds selected from screening of LPAAT-β inhibitors from different structural families can inhibit proliferation of numerous tumor cell lines in vitro. Both nude and immunocompetent mice can tolerate at least 100 mg/kg/day for 4-5 days of the 6-chloro-N,N'-diphenyl-[1,3,5]triazine-2,4-diamine maintaining body weight and overall health with no discernable gross pathology. This compound can inhibit the growth of numerous tumor models in mice and may be a tumor-static compound.

III. LPAAT-β Inhibitors.

In one aspect, the compounds of the present invention relate to triazines of the Formula:

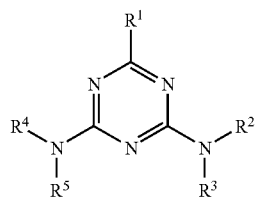

wherein, $R^1$ is halo, hydroxy, alkylmercapto, mercapto, alkoxy, aryloxy or substituted amino;

$R^2$, $R^3$, $R^4$ and $R^5$, each of which may be same or different, are hydrogen, alkyl, substituted alkyl, alkenyl, alkynyl, aryl or substituted aryl; or $R^2$ and $R^3$ or $R^4$ and $R^5$, together with the nitrogen to which they are attached, form a piperidine, piperazine, or a morpholine ring; or pharmaceutically acceptable salts thereof.

As used herein, "alkyl" refers to straight- or branched-chain hydrocarbons having from 1 to 10 carbon atoms and more preferably 1 to 8 carbon atoms which includes, by way of example, methyl, ethyl, n-propyl, i-propyl, n-butyl, t-butyl and the like.

The term "alkyl" also refers to an "unsaturated alkyl" moiety, which means that it contains at least one alkene or alkyne moiety. "Alkene" or "alkenyl" refers to a group consisting of at least two carbon atoms and at least one carbon-carbon double bond. "Alkyne" or "alkynyl" refers to a group consisting of at least two carbon atoms and at least one carbon-carbon triple bond. The alkyl moiety, whether saturated or unsaturated, may be branched, non-branched, or cyclic.

"Substituted alkyl" refers to an alkyl group, preferably containing from 1 to 10 carbon atoms, having from 1 to 5 substituents including halogen, hydroxyl, alkyl, aryl or substituted amino. A preferred substituted alkyl group is trifluromethyl.

"Alkoxy" refers to the group "alkyl-O—" which includes, by way of example, methoxy, ethoxy, n-propoxy, i-propoxy, n-butoxy, t-butoxy and the like.

"Substituted amino" refers to the group —NRR, wherein each R group is independently selected from the group consisting of hydrogen, alkyl, substituted alkyl, cycloalkyl, aryl, substituted aryl, or the R groups can be joined together with the nitrogen to form a heterocyclic ring (e.g., piperidine, piperazine, or a morpholine ring).

"Aryl" refers to an unsaturated aromatic carbocyclic group of 6 to 14 carbon atoms having a single ring (e.g., phenyl) or multiple condensed rings (e.g., naphthyl or anthryl).

"Substituted aryl" refers to aryl group which are substituted with 1 to 3 substituents selected from hydroxy, alkyl, substituted alkyl, alkoxy, amino, aryl, —O—$(CH_2)_n$—O— (wherein n is an integer from 1 to 3), —$(CH_2)_m$— (wherein m is an integer from 3 to 5) or halogen.

"Cycloalkyl" refers to cyclic alkyl groups containing between 3 and 8 carbon atoms having a single cyclic ring including, by way of example, cyclopropyl, cyclobutyl, cyclopentyl, cyclooctyl and the like.

"Halogen" or "halo" refers to fluoro, chloro, bromo, iodo. Most preferred halogens are chloro and fluoro.

"Mercapto" refers to the group -SR wherein the R group is independently selected from the group consisting of hydrogen, alkyl, substituted alkyl, cycloalkyl, aryl or substituted aryl. The term "alkylmerecapto" refers to the group —SR when R is alkyl, substituted alkyl or cycloalkyl.

Compounds of the preferred embodiments of the present invention include those compounds in Table 1.

| CT Number | Structure | LPAATβ Colorimetric Assay $IC_{50}$ (nM) |
|---|---|---|
| 31867 | 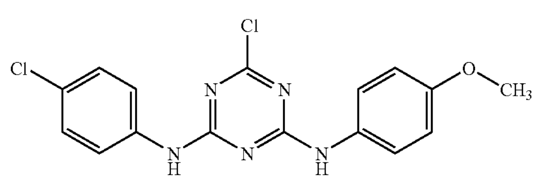 | 750 |
| 31942 | 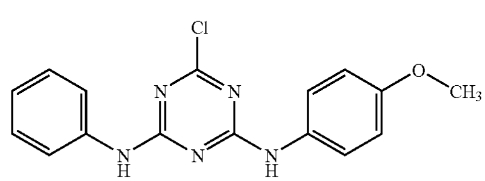 | 400 |

| CT Number | Structure | LPAATβ Colorimetric Assay IC$_{50}$ (nM) |
|---|---|---|
| 31978 | 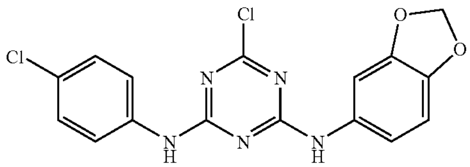 | 1,000 |
| 32028 | 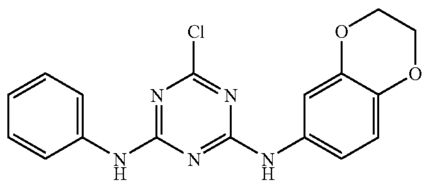 | 200 |
| 32042 | 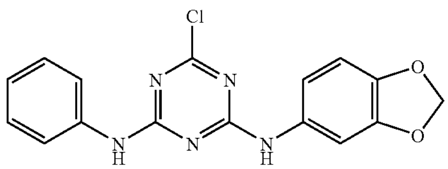 | 200 |
| 32099 | 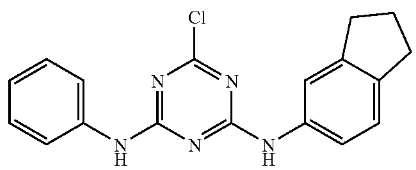 | 650 |
| 116988 | 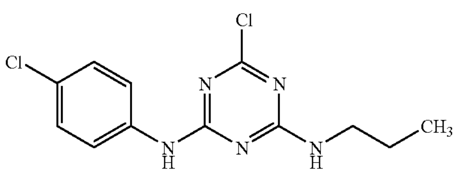 | 160 |
| 117147 | 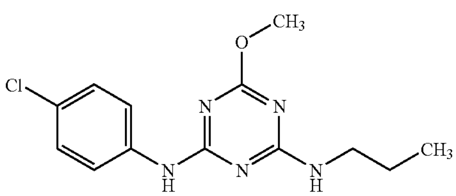 | 3,800 |
| 31888 | 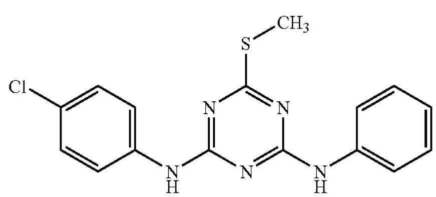 | 3,100 |

Preferred compounds include, but are not limited to, 6-chloro-N-(4-methoxy-phenyl)-N'-p-tolyl-[1,3,5]triazine-2,4-diamine, N-butyl-6-chloro-N'-(4-chlorophenyl)-[1,3,5]triazine-2,4-diamine, 6-chloro-N-isopropyl-N'-p-tolyl-[1,3,5]triazine-2,4-diamine, N-tert-butyl-6-chloro-N'-phenyl-[1,3,5]triazine-2,4-diamine, (4-chloro-6-morpholin-4-yl-[1,3,5]triazin-2-yl)-naphthalen-1-yl-amine, N-tert-butyl-6-chloro-N'-p-tolyl-[1,3,5]triazine-2,4-diamine, 6-chloro-N-cyclo-hexyl-N'-isopropyl-[1,3,5]triazine-2,4-diamine, 2-(4-chloro-6-phenylamino-[1,3,5]triazin-2-ylamino)-2-methyl-propan-1-ol, 6-chloro-N-isopropyl-N'-phenyl-[1,3,5]triazine-2,4-diamine, 6-chloro-N-(4-chloro-phenyl)-N'-cyclohexyl-[1,3,5]triazine-2,4-diamine, N-allyl-6-chloro-N'-cyclohexyl-[1,3,5]triazine-2,4-diamine, 2-(chloro-6-phenylamino-[1,3,5]triazin-2-ylamino)-ethanol, N-tert-butyl-6-chloro-N'-cyclopentyl-[1,3,5]triazine-2,4-diamine, 6-chloro-N-(4-methoxyphenyl)-N'-phenyl-[1,3,5]triazine-2, 4-diamine, N-benzo[1,3]dioxol-5-yl-6-chloro-N'-(4-chlorophenyl)-[1,3,5]triazine-2,4-diamine, 6-chloro-N-(2,3-dihydrobenzo[1,4]dioxin-6-yl)-N'-phenyl-[1,3,5]triazine-2,4-diamine, N-benzo[1,3]dioxol-5-yl-6-chloro-N'-phenyl-[1,3, 5]triazine-2,4-diamine, 6-chloro-N-indan-5-yl-N'-phenyl-[1, 3,5]triazine-2,4-diamine, 6-chloro-N-(4-chloro-phenyl)-N'-propyl-[1,3,5]triazine-2,4-diamine, N-(4-chloro-phenyl)-6-methoxy-N'-propyl-[1,3,5]triazine-2,4-diamine and N-(4-chloro-phenyl)-6-methylsulfanyl-N'-phenyl-[1,3,5]triazine-2,4-diamine.

Most preferred compounds include, but are not limited to, 6-chloro-N,N'-diphenyl-[1,3,5]triazine-2,4-diamine, N-tert-butyl-6-chloro-N'-(4-chlorophenyl)-[1,3,5]triazine-2,4-diamine, 6-chloro-N-(4-chlorophenyl)-N'-(4-methoxyphenyl)-[1,3,5]triazine-2,4-diamine, 6-chloro-N-(4-chlorophenyl)-N'-phenyl-[1,3,5]-triazine-2,4-diamine.

The compounds of the preferred embodiments of the present invention inhibit LPAAT-β and thereby inhibit cell proliferation. Therefore, the compounds of the preferred embodiments of the present invention may be useful in the treatment of cancer. The types of cancer that may be treated with the compounds of the preferred embodiments of the present invention include, but are not limited to, prostate, breast, lung, ovarian, brain, cervical, colon or bladder cancer, and not limited to tumor cells expressing high levels of LPAAT-β as evidenced by the decrease in NIH/3T3 Ki-ras tumor cell growth in vitro and in vivo when treated with, 6-chloro-N,N'-diphenyl-[1,3,5]triazine-2,4-diamine.

IV. Pharmacological Compositions, Therapeutic and Other Applications.

The compound of the present invention, or its pharmaceutically acceptable salt, can be administered to a human patient per se, or in pharmacological compositions where it is mixed with pharmaceutically acceptable carriers or excipient(s). Techniques for formulation and administration of drugs may be found in "Remington's Pharmaceutical Sciences," Mack Publishing Co., Easton, Pa., latest edition.

A. Routes of Administration.

Suitable routes of administration may include, without limitation, oral, rectal, transmucosal or intestinal administration or intramuscular, subcutaneous, intramedullary, intrathecal, direct intraventricular, intravenous, intraperitoneal or intranasal injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

B. Composition/Formulation.

Pharmacological compositions of the compounds and the pharmaceutically acceptable salts thereof are preferred embodiments of this invention. Pharmacological compositions of the present invention may be manufactured by processes well known in the art; e.g., by means of conventional mixing, dissolving, granulating, dragee-making, levigating, emulsifying, encapsulating, entrapping or lyophilizing processes.

Pharmacological compositions for use in accordance with the present invention thus may be formulated in a conventional manner using one or more pharmaceutically acceptable carriers comprising excipients and auxiliaries which facilitate processing of the active compounds into preparations which can be used pharmaceutically. Proper formulation is dependent upon the route of administration chosen.

For injection, the compounds of the invention may be formulated as sterile aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmacological preparations for oral use can be made with the use of a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmacological compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmacological compositions for parenteral administration include sterile aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation (see, for example, U.S. Pat. No. 5,702,717 for a biodegradable depot for the delivery of a drug). Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The pharmacological compositions herein also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds of the invention that inhibit LPAAT-β may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate, etc. formed by the reaction of an amino group with the appropriate acid.

C. Dosage.

Pharmacological compositions suitable for use in the present invention include compositions wherein the active ingredients are contained in an amount effective to achieve its intended purpose.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of LPAAT-β activity). Such information can be used to more accurately determine useful doses in humans.

Toxicity and therapeutic efficacy of the compounds described herein can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see e.g., Fingl, et al., in "The Pharmacological Basis of Therapeutics," (1975), Chapter 1, pp. 1).

Dosage amount and interval may be adjusted individually to provide plasma levels of the active moiety which are sufficient to maintain LPAAT-β inhibitory effects, or minimal effective concentration (MEC). The MEC will vary for each compound but can be estimated from in vitro data; e.g., the concentration necessary to achieve 50-90% inhibition of LPAAT-β using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner, of administration and the judgment of the prescribing physician. An exemplary systemic daily dosage is about 5 to about 200 mg/kg of body weight. Normally, from about 10 to about 100 mg/kg of body weight of the compounds of the preferred embodiments of the present invention, in one or more dosages per day, is effective to obtain the desired results. One of ordinary skill in the art can determine the optimal dosages and concentrations of the compounds of the preferred embodiments of the present invention with only routine experimentation.

The compounds of the preferred embodiments of the present invention are substantially pure and preferably sterile. The phrase "substantially pure" encompasses compounds created by chemical synthesis and/or compounds substantially free of chemicals which may accompany the compounds in the natural state, as evidenced by thin layer chromatography (TLC) or high performance liquid chromatography (HPLC).

D. Other Applications

The compounds of the preferred embodiments of the present invention may be employed not only for therapeutic purposes, but also as aids in performing research in vitro. For example, the compounds of the preferred embodiments of the present invention may be used to study biochemical pathways that would require the inhibition of LPAAT-β to elevated levels of LPA. Inhibition of LPAAT-β may result in the prolonged or limited activity of biochemical pathways that depend on, or respond to, elevated levels of LPA.

Additionally, a cell culture medium comprising the compounds of the preferred embodiments of the present invention is within the scope of the invention.

V. Assays for LPAAT-β DNA, RNA and Protein.

DNA molecules encoding the human LPAAT-β gene, or fragments thereof, can be used to detect the level of LPAAT-β gene expression in tissue samples. Such a detection method can be used, for example, to compare the amount of LPAAT-β RNA in a sample obtained from normal tissue and in a sample isolated from methotrexate-resistant tumor tissue. The presence of relatively low levels of LPAAT-β RNA in the tumor sample would indicate that methotrexate resistance is due, at least in part, to underexpression of the LPAAT-β gene.

In testing a tissue sample for LPAAT-β RNA using a nucleic acid hybridization assay, RNA can be isolated from tissue by sectioning on a cryostat and lysing the sections with a detergent such as SDS and a chelating agent such as EDTA, optionally with overnight digestion with proteinase K. Such tissue may be obtained by biopsy. A preferred quantity of tissue is in the range of 10-100 milligrams. Protein may be removed by phenol and chloroform extractions, and nucleic acids are precipitated with ethanol. RNA may be isolated by chromatography on an oligo dT column and then eluted from the column. Further fractionation can also be carried out according to methods well known to those of ordinary skill in the art.

A number of techniques for molecular hybridization are used for the detection of DNA or RNA sequences in tissues. When large amounts of tissue are available, analysis of hybridization kinetics provides the opportunity to accurately quantitate the amount of DNA or RNA present, as well as to distinguish sequences that are closely related but not identical to the probe. Reactions are run under conditions of hybridization ($T_m - 25°$ C.) in which the rate of re-association of the probe is optimal. Wetmur et al., *J. Mol. Biol.* 31:349 (1968). The kinetics of the reaction are second order when the sequences in the tissue are identical to those of the probe; however, the reaction exhibits complex kinetics when probe sequences have partial homology to those in the tissue. Sharp et al., *J. Mol. Biol.* 86:709 (1974).

The concentration of probe to cellular RNA is determined by the sensitivity desired. To detect one transcript per cell would require about 100 pg of probe per mg of total cellular DNA or RNA. The nucleic acids are mixed, denatured, brought to the appropriate salt concentration and temperature, and allowed to hybridize for various periods of time. The rate of reassociation can be determined by quantitating the amount of probe hybridized either by hydroxyapatite chromatography (Britten et al., *Science* 161:529 (1968)) or by S1 nuclease digestion (Sutton, *Biochim. Biophys. Acta* 240:522 (1971)).

Another method of hybridization is the Northern Blot technique. The particular hybridization technique is not essential to the invention, and any technique commonly used in the art is within the scope of the present invention. Typical probe technology is described in U. S. Pat. No. 4,358,535, incorporated by reference herein. For example, hybridization can be carried out in a solution containing 6×SSC (10×SSC: 1.5 M sodium chloride, 0.15 M sodium citrate, pH 7.0), 5× Denhardt's (1× Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C.

The aforementioned hybridization assays are particularly well suited for preparation and commercialization in kit form, the kit comprising a carrier means compartmentalized to receive one or more container means (vial, test tube, etc.) in close confinement, with each container means comprising one of the separate elements to be used in hybridization assay. For example, there may be a container means containing LPAAT-β DNA molecules suitable for labeling by "nick translation," or containing labeled LPAAT-β DNA or labeled LPAAT-β RNA molecules. Further container means may contain standard solutions for nick translation of DNA comprising DNA polymerase I/DNase I and unlabeled deoxyribonucleotides.

Antibodies to human LPAAT-β protein can be obtained using the product of an LPAAT-β expression vector as an antigen. The preparation of polyclonal antibodies is well-known to those of skill in the art. See, for example, Green et al., "Production of Polyclonal Antisera," in *Immunochemical Protocols* (Manson, ed.), pp. 1-5 (Humana Press 1992). Alternatively, an LPAAT-β antibody of the present invention may be derived from a rodent monoclonal antibody (MAb). Rodent monoclonal antibodies to specific antigens may be obtained by methods known to those skilled in the art. See, for example, Kohler and Milstein, *Nature* 256:495, 1975, and Coligan et al. (eds.), *Current Protocols in Immunology*, 1:2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of techniques that are well known in the art. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in *Methods in Molecular Biology*, 10:79 (Humana Press, Inc. 1992). A LPAAT-β antibody may also be derived from a subhuman primate antibody. General techniques for raising therapeutically useful antibodies in baboons may be found, for example, in Goldenberg et al., International Patent Publication No. WO 91/11465 (1991), and in Losman et al., *Int. J Cancer* 46:310 (1990).

Alternatively, a therapeutically useful LPAAT-β antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l. Acad. Sci. USA* 86:3833 (1989). Techniques for producing humanized MAbs are described, for example, by Jones et al., *Nature* 321:522 (1986); Riechmann et al., *Nature* 332:323 (1988); Verhoeyen et al., *Science* 239:1534 (1988); Carter et al., *Proc. Nat'l. Acad. Sci. USA* 89:4285 (1992); Sandhu, Crit. Rev. *Biotech.* 12: 437 (1992); and Singer et al., *J. Immun.* 150:2844 (1993), each of which is hereby incorporated by reference.

As an alternative, a LPAAT-β antibody of the present invention may be derived from human antibody fragments isolated from a combinatorial immunoglobulin library. See, for example, Barbas et al., *METHODS: A Companion to Methods in Enzymology* 2:119 (1991); and Winter et al., *Ann. Rev. Immunol.* 12:433 (1994) which are incorporated herein by reference. Cloning and expression vectors that are useful for producing a human immunoglobulin phage library can be obtained, for example, from STRATAGENE Cloning Systems (La Jolla, Calif.). In addition, a LPAAT-β antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immun.* 6:579 (1994).

Having now generally described this invention, the same will be understood by reference to the following examples which are provided herein for purposes of illustration only and are not intended to be limiting unless otherwise specified.

EXAMPLE 1

Production of Recombinant LPAAT-β for Various Assays

For the construction of Baculovirus expression vectors, the full-length human LPAAT-β cDNA was amplified by PCR from the DNA template pCE9.LPAAT-β (West et al., *DNA Cell Biol.* 16:691-701 (1997)) using the primers 5'-TGATATCCGA AGAAGATCTT ATGGAGCTGT GGC-CGTGTC-3' (olpb1F; SEQ ID NO:3) and 5'-CAGGCTCTAG ACTACTGGGC CGGCTGCAC-3' (olpb1R; SEQ ID NO:4). The ~870 bp fragment generated was reamplified by PCR using the primers 5° CCTACGTCG ACATGGAACA AAAATTGATA TCCGAAGAAG ATC-3' (olpb2F; SEQ ID NO:5) and 5'-CAGGCTCTAG ACTACTGGGC CGGCTG-CAC-3' (olpb1R; SEQ ID NO:6). The ~890 bp fragment generated was then cleaved with Sal I and Xba I for insertion into pFastBac™ HTc vector (Life Technologies, Gaithersberg, Md.) between the Sal I and Xba I sites for the generation of the plasmid pFB.LPAAT-β. This plasmid was then transformed into *E. coli* DH10Bac™ (Life Technologies, Gaithersberg, Md.) for the generation of recombinant Bacmid DNA for transfection into HighFive (Invitrogen, San Diego, Calif.) or SF9 insect cells for the production of recombinant Baculovirus stocks using the protocol described in the Bac-to-Bac® Baculovirus Expression System (Life Technologies, Gaithersberg, Md.), a eukaryotic expression system for generating recombinant baculovirus through site- specific transposition in *E. coli*. Viral stocks harvested from the transfected cells can then be used to infect fresh insect cells for the subsequent expression of LPAAT-β fusion protein with a poly-histidine tag and a myc-epitope near its N-terminus. The membrane fraction from these Sf9 cells would be the source of LPAAT enzyme.

EXAMPLE 2

Preparation of Cell Membranes from Sf9 Cells

For the preparation of membranes From Sf9 Cells, all steps are performed on ice or at 4° C. Sf9 cell pellets (~$10^8$ cells) were thawed and resuspended in 1-2 ml of buffer A (20 mM Hepes, pH 7.5, 1 mM DTT, 1 mM EDTA, 20% w/v glycerol, 1 mM Benzamidine, 1 µg/ml soybean trypsin inhibitor (SBTI), 1 µg/ml pepstatin A) w/o DTT but with 1 mM Pefabloc. The cells were lysed by sonication using a Branson Sonifier at output=2, duty cycle=2, 10 pulses each at 10 s. with the tip of small sonicator probe submerged but not touching the walls. DTT was then added to 1 mM from a 1 M stock. The samples were centrifuged at 1500 rpm for 5 min. The low speed supernatant was saved and centrifuged (TLA 100.3 rotor, polycarbonate tubes, 2 ml/tube or 1.5 ml/tube minimum) at 100000×g for 1 hr. The high speed pellet was resuspend in Buffer A with a probe sonicator (10 pulses @ output #2 and duty cycle 20%) as a source of LPAAT enzyme.

EXAMPLE 3

Assay of LPAAT-β Activity

Figure 7:
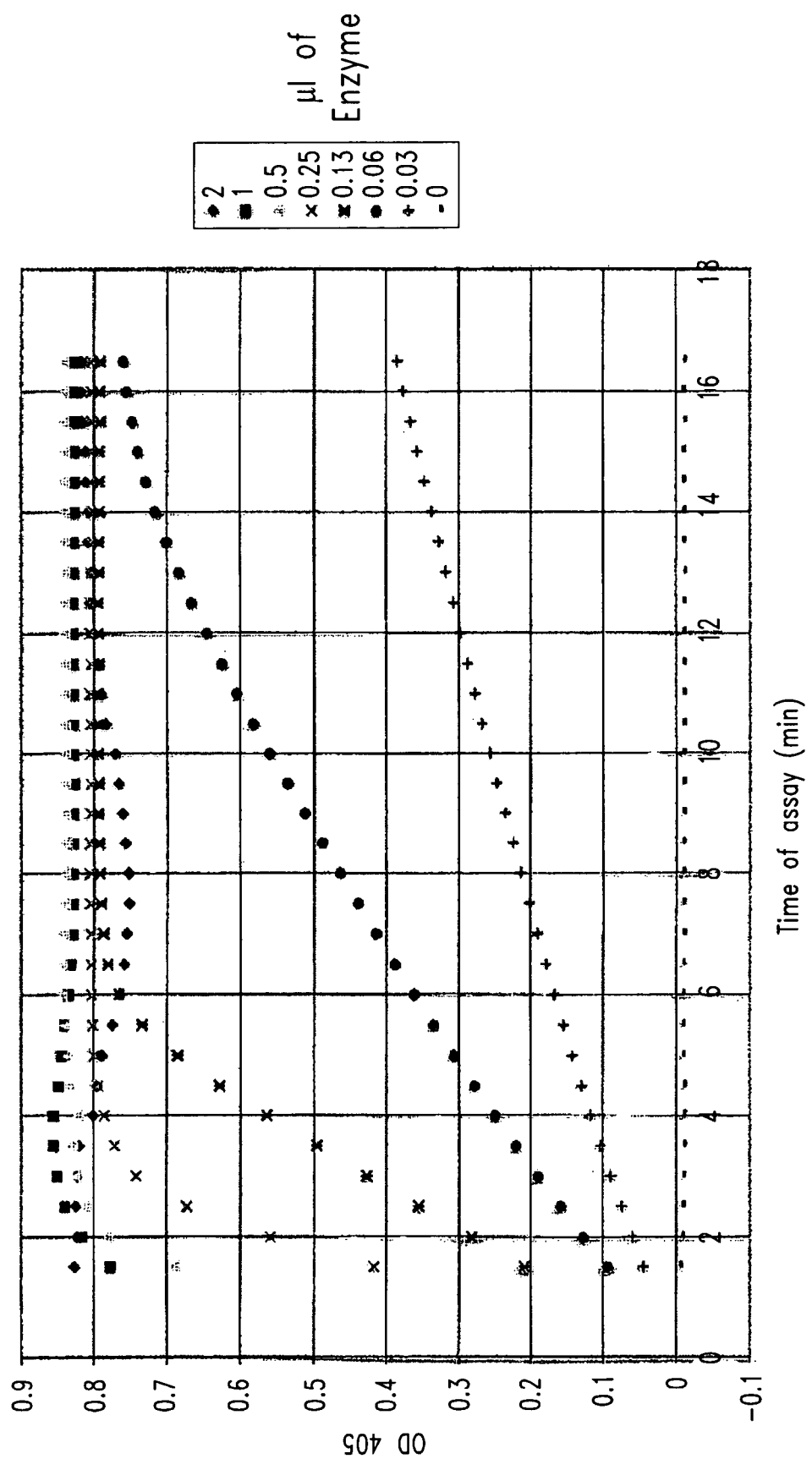
FIG. 7 shows a colorimetric assay whose time course of color development is dependent on LPAAT enzyme.
Figure 8:
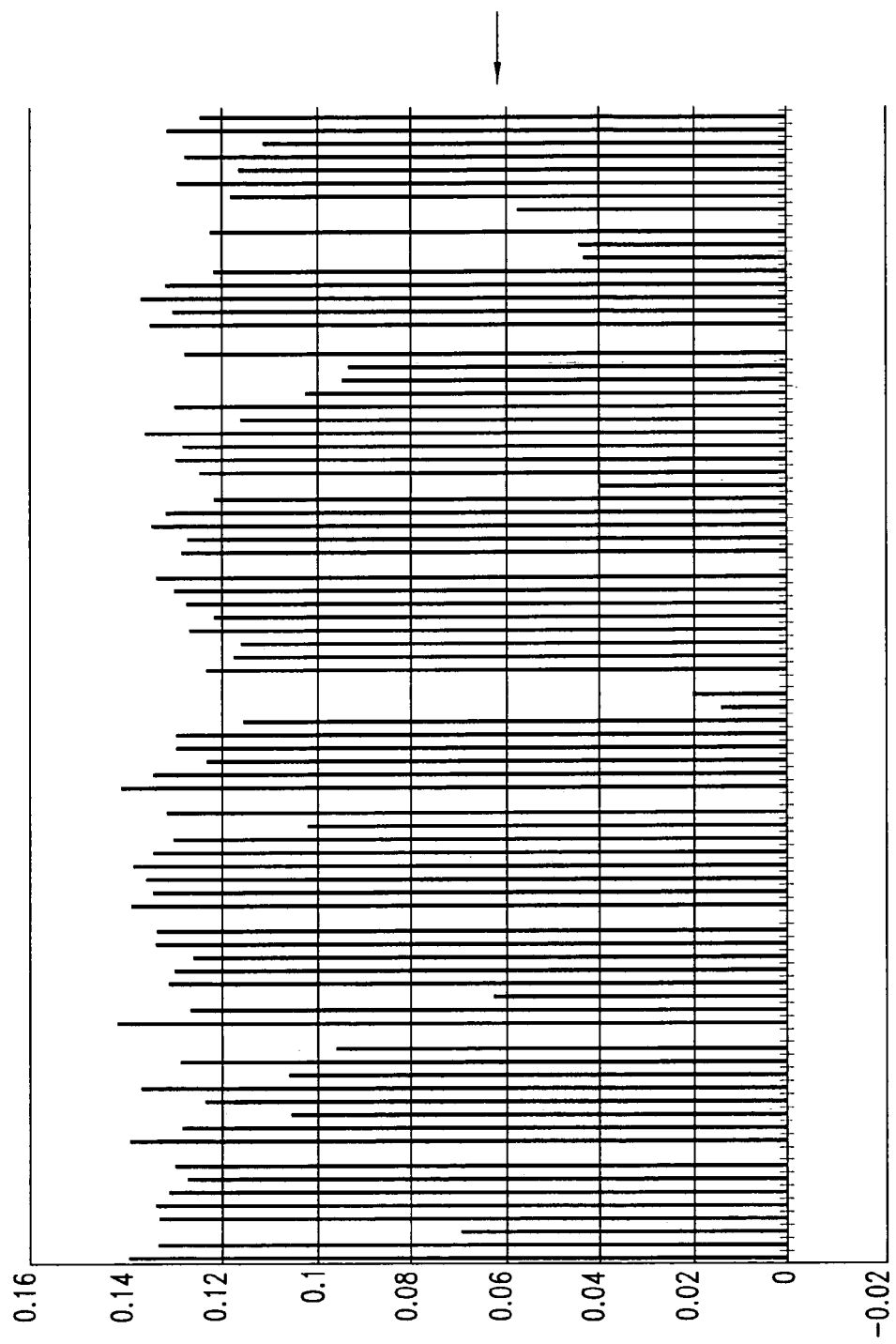
FIG. 8 shows the result from assaying a plate of various compounds at 16 mM.

LPAAT-β catalyzes the transfer of an acyl group from a donor such as acyl-CoA to LPA. The transfer of the acyl group from acyl-CoA to LPA leads to the release of free CoA, which can be reacted with the thiol reagent, 5,5'-dithiobis(2-nitrobenzoic acid) (DTNB). The reaction between DTNB and the free sulfhydryl group from CoA generates a yellow-colored product, 3-carboxylato-4-nitrothiophenolate (CNP), that absorbs at 413 nm. LPAAT-β derived from Sf9 cell membrane overexpressing LPAAT-β were resuspended in HEPES saline buffer (20 mM HEPES pH 7.5, 150 mM NaCl), 1 mg/ml BSA and 72 µl aliquots were distributed into 96-well microtiter plates. 8 µl of compound of interest at 200 µM dissolved in 100% DMSO was added into each well. 20 µl of 1 mM 18:1-CoA and 1 mM sn-1-18: 1 lysoPA was then added to each well to initiate the reaction and allowed to run at room temperature for 25 min. 100 µl of 1 mM DTNB in 100% ethanol was then added to each well to quench the reaction and for color development. The absorbance at 405 nm, measured using a spectrophotometer plate reader, is proportional to the activity of LPAAT-β in the sample. This colorimetric assay was used for the high throughput screening of LPAAT inhibitors. Compounds that showed >50% inhibition of the change in absorbance at 405 nm compared to control were selected for a secondary assay. FIG. 7 shows an example of the calorimetric assay of which the time course of color development is dependent on the amount of LPAAT enzyme added. FIG. 8 shows an example of the results obtained from assaying a plate of various compounds at 16 µM. Compounds that gave a reading of less than 0.06 arbitrary units (indicated by arrow on right margin) were selected for further study.

A secondary assay for LPAAT activity in cell extracts based on either the conversion of fluorescent NBD-LPA to NBD-PA (West, et al., *DNA Cell Biol.* 6: 691-701, 1997) or [$^{14}$C]LPA to [$^{14}$C]PA using TLC analysis was used to screen compounds that showed >50% inhibition of LPAAT activity in the primary calorimetric assay. The radiometric assay was carried out in Sf9 cell membrane overexpressing LPAAT-β resuspended in HEPES-saline buffer, pH 7.5, 1 mg/ml BSA, 1 mM EDTA and 200 µM [$^{14}$C]18:1-CoA and 200 µM sn-1-18:1 lysoPA. The samples were incubated 7 min at 37° C. extracted into organic solvent (CHCl$_3$/CH$_3$OH/HCl at 33/66/1), before loading onto TLC plates. A more detailed protocol for the radiometric assay is described below:

Specifically, this LPAAT assay is a modification of the acyltransferase assay published previously (Hollenback and Glomset, *Biochemistry* 37: 363-376 (1999)).

1. The basic assay, in a total vol of 50 µl, employs a solution of substrates and the protein sample. Total assay volume, as well as the volume of each solution, can be changed to fit an experiment. In addition, other compounds, ex inhibitors and activators, can be included in the assay as well.
2. To prepare the solution of substrates:
   a. Stocks of Hepes (pH 7.5), NaCl, EDTA, BSA and acyl-CoA (from Serdery or Sigma) are mixed with water to make the appropriate concentration of each compound. This can be varied from assay-to-assay, but the final reaction mix is about 50 mM Hepes, 100 mM NaCl, 1 mM EDTA, 1 mg/ml BSA and 0-400 µM acyl-CoA.
   b. The lysoPA (from Avanti) is typically stored in chloroform and the $^{14}$C-labeled acyl-CoA (from Amersham) is typically stored in water/ethanol=1:1. Appropriate amounts of each solution are added the to a 12×75 mm borosilicate glass test tube and dry the solvent under N$_2$ or Ar. An appropriate volume of the solution prepared in 2a is added to the iysoPA and $^{14}$C-labeled acyl-CoA. The lipids are resuspend by sonication for 15 sec in a bath sonicator. The resulting suspension is then incubated (with occasional gentle vortexing) for about 10 minutes at room temp. The sn-1-16:0 lysoPA may require brief warming of the solvent to solubilize it. The concentration of lysoPA and $^{14}$C-labeled acyl-CoA can vary, but typically the final lysoPA concentration ranges between 0 and 400 µM and the $^{14}$C-labeled acyl-CoA specific activity ranges between 0.5 and 2 Ci/mol.
3. Protein sample: varies from experiment-to-experiment.
4. The assay is performed by mixing the components in 12×75 mm borosilicate glass test tubes (the order of addition does not matter unless indicated) and incubating at 37° C. for 5 to 10 minutes such that the assay within the linear range for time and protein.
5. The reaction is quenched by adding 1.3 ml of chloroform/methanol/HCl=48/51/0.7 and vortexing. 10 µl of carrier solution is then added (3 mg/ml each PA, ex. 16:0-18:1, and lysoPA, ex sn-1-18:1, in chloroform). Two phases are formed by adding 0.3 ml of water to each tube and vortexing.
6. The sample is centrifuged for 3 minutes at 1000×g, the upper (aqueous/methanol) phase is aspirated and the lower phase is dried under nitrogen.
7. Thin layer chromatography:
   a. The dried samples are resuspended in 50 µl of chloroform and a 15 µl aliquot is immediately spotted on an Analtech silica gel 60 HP-TLC plate (10×20 cm).
   b. Plates are developed in chloroform/methanol/acetic acid/water=85/12.5/12.5/3 (takes about 15 min) and dried.
   c. To be able to convert pixel volume (determined by the Storm phosphor imager, see step 8b) into cpm, cpm standard curve must be generated on the plate. $^{14}$C-labeled oleate dilutions in chloroform are made for this purpose. Four stocks (50 cpm/µl to 800 cpm/µl) are made and 2 µl of a different concentration are spotted in each corner of the plate (where previously there was no radioactivity).
   d. For quality control purposes, the plates are stained with primuline and scanned with the Storm (blue chemilluminescence mode).

The PA and lysoPA bands are easily detected in this system because of the carrier added in step 5. PA and lysoPA have respective Rf's of about 0.63 and 0.21.
8. Quantitating activity:
   a. The plates are then wrapped in saran wrap and exposed to a freshly blanked phosphor screen overnight (longer exposures can also be done to increase the signal).
   b. The screens are scanned (Phosphorimager mode), and LPAAT activity is determined by quantifying the pixels in the band comigrating with PA standard versus the standard curve generated from the cpm standards that were spotted in step 7c.

Figure 9:
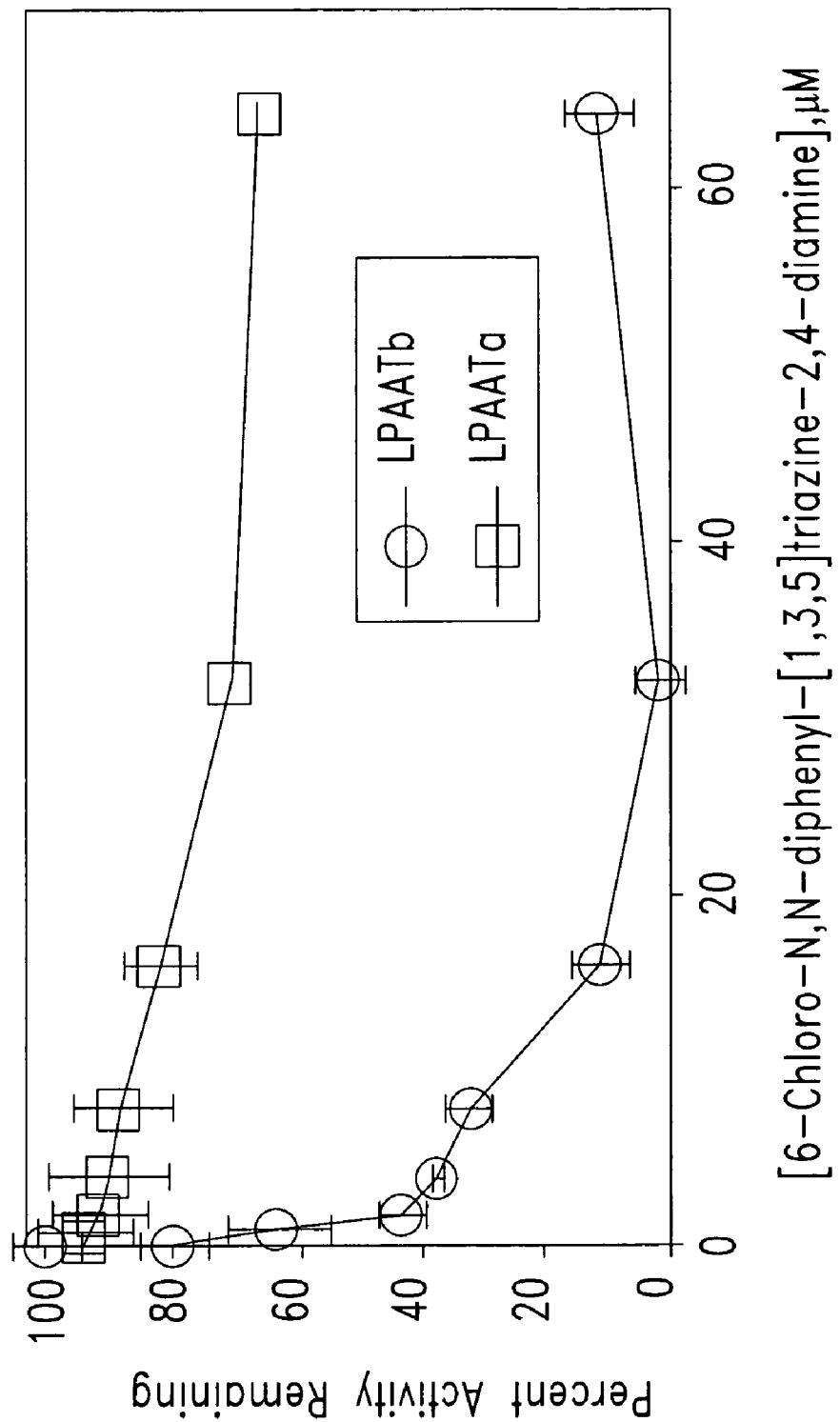
FIG. 9 shows the results of the effects of a compound selected from secondary screening on LPAAT-β activity and LPAAT-α activity.

FIG. 9 shows examples of a compound, namely, 6-chloro-N,N'-diphenyl-[1,3,5]triazine-2,4-diamine, selected from the secondary screening that exhibit concentration-dependent inhibition of LPAAT-β activity (○). Moreover, these compounds have minimal effect on LPAAT-α activity (□), suggesting they are isoform-specific inhibitors.

EXAMPLE 4

Triazines of the preferred embodiments of the present invention were synthesized by one of two methods. Symmetrically substituted triazines were synthesized by the addition of two equivalents of the appropriate amino compound, in the presence of diisopropylethylamine, to cyanuric chloride. Non-symmetrical triazines were synthesized in a stepwise fashion by the sequential addition of the amino compound in the presence of potassium carbonate with isolation of the intermediate mono-amino-dichlorotriazine.

A. Method 1: Synthesis of Symmetrical Triazines.

Synthesis of 6-chloro-N,N'-diphenyl-[1,3,5]triazine-2,4-diamine (CT-113020)

To a mixture of cyanuric chloride (5.07 g, 27.5 mmol) and acetonitrile (60 ml), cooled in an ice bath, was added a solution of aniline (5.3 ml, 58.2 mmol) and diisopropylethylamine (10.5 ml, 60.3 mmol) in acetonitrile (15 ml) over 30 minutes. After stirring at room temperature for 20 hours, the mixture was filtered. The solid was washed with ethyl acetate (4×25 ml), suspended in water (50 ml), stirred for 1 hour, filtered, washed with water, and dried under vacuum to give 6-chloro-N,N'-diphenyl-[1,3,5]triazine-2,4-diamine (3.97 g, 48% yield) as a white solid. $^1$H NMR (d$_6$-DMSO) δ 7.61 (2H, br s), 7.28-7.37 (4H, m), 7.05-7.11(4H, m). $^{13}$C NMR (d$_6$-DMSO) δ 167.7, 164.0, 138.5, 128.4 124.5, 121.3.

B. Method 2: Synthesis of Unsymmetrical Triazines.

Synthesis of 6-chloro-N-(4-chlorophenyl)-N'-phenyl-[1,3,5]triazine-2,4-diamine (CT-116433)

To a mixture of cyanuric chloride (5.15 g, 27.9 mmol), potassium carbonate (3.98 g, 28.8 mmol) and 18-crown-6 (158 mg, 0.60 mmol) in toluene (40 ml), cooled in an ice bath, was added a solution of 4-chloroaniline (3.61 g, 28.3 mmol) in toluene (20 ml) over 15 minutes. After stirring at room temperature for 20 hours, the mixture was treated with ethyl acetate (60 ml) and filtered through a pad of celite under suction. The filtrate was concentrated under vacuum and recrystallized (chloroform) to give (4-chloro-phenyl)-(4,6-dichloro-[1,3,5]triazin-2-yl)-amine (4.06 g, 53% yield) as a white solid. $^1$H NMR (d$_6$-DMSO) δ 11.23 (1H, s), 7.62 (2H, d, J=9 Hz), 7.47(2H, d, J=9 Hz). $^{13}$C NMR (d$_6$-DMSO) δ 169.5, 168.5, 163.6, 135.7, 128.6, 122.5, ESMS m/z 273 (M−H)$^-$.

To a mixture of (4-chloro-phenyl)-(4,6-dichloro-[1,3,5]triazin-2-yl)-amine (3.97 g, 14.4 mmol), potassium carbonate (2.20 g, 15.9 mmol) and 18-crown-6 (46 mg, 0.17 mmol) in toluene (25 ml), cooled in an ice bath, was added a solution of aniline (1.4 ml, 15.4 mmol) in toluene (10 ml) over 15 minutes. After stirring at room temperature for 24 hours, the mixture was treated with ethyl acetate (35 ml) and filtered through a pad of celite under suction. The filtrate was concentrated under vacuum and the residue was recrystallized (chloroform) to give 6-Chloro-N-(4-chlorophenyl)-N'-phenyl-[1,3,5]triazine-2,4-diamine (2.20 g, 46% yield) as a white solid. $^1$H NMR (d$_6$-DMSO) δ 10.1-10.4 (2H, br s), 7.5-7.8 (4H, br s), 7.3-7.5 (4H, m), 7.15-7.05 (1H, m), ESMS m/z 330 (M–H)$^-$.

EXAMPLE 5

Synthesis of 6-chloro-N-(4-chlorophenyl)-N'-(4-methoxy-phenyl)-[1,3,5]triazine-2,4-diamine (CT-31867)

The reaction of (4-chloro-phenyl)-(4,6-dichloro-[1,3,5]triazin-2-yl)-amine with p-anisidine, according to method 2, gave 6-chloro-N-(4-chlorophenyl)-N'-(4-methoxyphenyl)-[1,3,5]triazine-2,4-diamine (51 mg, 62%): $^1$H NMR (CDCl$_3$) 7.21-7.50 (6H, m), 6.91(2H, d, J=11 Hz), 3.85 (3H, s).

EXAMPLE 6

Synthesis of 6-chloro-N-(4-methoxyphenyl)-N'-phenyl-[1,3,5]triazine-2,4-diamine (CT-31942)

To a solution of 2-(4-methoxyphenyl)amino-4,6-dichloro-1,3,5-triazine (57 mg, 0.21 mmoles) in acetonitrile (0.5 ml) was added a solution of aniline (0.021 ml, 0.23 mmoles) and diisopropylethylamine (0.05 ml, 0.29 mmoles) in acetonitrile (0.5 ml). After stirring for 24 hours, the mixture was concentrated under vacuum and the residue was dissolved in ethyl acetate (10 ml). The solution was washed with a solution composed of saturated aqueous sodium chloride solution and 1 M hydrochloric acid (1:1, 2×10 ml), dried over sodium sulfate, filtered, and concentrated under vacuum. The residue was purified by flash chromatography on silica gel eluting with 10% ethyl acetate-hexane to provide CT-31942 (38 mg, 57% yield). $^1$H NMR (d$_6$-DMSO) δ 10.00-10.22 (m, 2H), 7.26-7.82 (m, 6H), 7.01-7.10 (m, 1H), 6.91 (d, J=9 Hz, 2H), 3.74 (s, 3H).

EXAMPLE 7

Synthesis of N-benzo[1,3]dioxol-5-yl-6-chloro-N'-(4-chlorophenyl)-[1,3,5]triazine-2,4-diamine (CT-31978)

The reaction of 4,6-dichloro-N-(4-chlorophenyl)-[1,3,5]triazine-2-amine with 3,4-methylenedioxyaniline using the method described for the synthesis of CT-116433 provided CT-31978 (56 mg, 65% yield). $^1$H NMR (d$_6$-DMSO) δ 10.08-10.37 (m, 2 H), 7.58-7.87 (m, 2H), 7.21-7.40 (m, 3H), 6.85-7.03 (m, 2H), 6.00 (s, 2H).

EXAMPLE 8 synthesis of 6-chloro-N-(2,3-dihydrobenzo[1,4]dioxin-6-yl)-N'-phenyl-[1,3,5]triazine-2,4-diamine (CT-32028)

To a solution of 4,6-dichloro-N-phenyl-[1,3,5]triazine-2-amine (95 mg, 0.39 mmoles) in tetrahydrofuran (2 ml) was added a solution of 1,4-benzodioxan-6-amine (64 mg, 0.42 mmoles) and triethylamine (0.07 ml, 0.50 mmoles) in tetrahydrofuran (0.5 ml). After stirring for 24 hours, the mixture was concentrated under vacuum and the residue was dissolved in ethyl acetate (10 ml). The solution was washed with a solution composed of saturated aqueous sodium chloride solution and 1 M hydrochloric acid (1:1, 2×10 ml), dried over sodium sulfate, filtered, and concentrated under vacuum. The residue was purified by flash chromatography on silica gel eluting with 25% ethyl acetate-hexanes to provide CT-32028 (97 mg, 69% yield). $^1$H NMR (d$_6$-DMSO) δ 9.88-10.28 (m, 2H), 7.60-7.85 (m, 2H), 7.20-7.40 (m, 3H), 6.96-7.10 (m, 2H), 6.77-6.81 (m, 1H), 4.21 (s, 4H).

EXAMPLE 9

Synthesis of N-benzo[1,3]dioxol-5-yl-6-chloro-N'-phenyl-[1,3,5]triazine-2,4-diamine (CT-32042)

The reaction of 4,6-dichloro-N-phenyl-[1,3,5]triazine-2-amine with 3,4-methylenedioxyaniline using the method described for the synthesis of CT-32028 provided CT-32042 (51 mg, 42% yield). $^1$H NMR (d$_6$-DMSO) δ 10.05-10.29 (m, 2H), 7.57-7.80 (m, 2H), 7.21-7.42 (m, 3H), 6.80-7.13 (m, 3H), 6.03 (s, 2H).

EXAMPLE 10

Synthesis of 6-chloro-N-indan-5-yl-N'-phenyl-[1,3,5]triazine-2,4-diamine (CT-32099)

The reaction of 4,6-dichloro-N-phenyl-[1,3,5]triazine-2-amine with 5-aminoindan using the method described for the synthesis of CT-32028 provided CT-32099 (36 mg, 37% yield). $^1$H NMR (d$_6$-DMSO) δ 10.15-10.28 (m, 2H), 7.56-7.72 (m, 3H), 7.05-7.39 (m, 5H), 2.75-90 (m, 4H), 1.94-2.09 (m, 2H).

EXAMPLE 11

Synthesis of 6-chloro-N-2-(4-chlorophenyl)-N-4-propyl-[1,3,5]triazine-2,4-diamine (CT-116988)

The reaction of 4,6-dichloro-N-(4-chlorophenyl)-[1,3,5]triazine-2-amine with propylamine using the method described for the synthesis of CT-116433 provides CT-116988.

EXAMPLE 12

Synthesis of N-(4-chlorophenyl)-6-methoxy-N'-propyl-[1,3,5]triazine-2,4-diamine (CT-117147)

A mixture of CT-116988 and sodium methoxide (3.0 molar equivalents) in methanol is heated at reflux for 18 hours. After cooling to room temperature, the reaction mixture is concentrated under vacuum. The residue is suspended in ethyl acetate and washed with water. The ethyl acetate phase is dried over sodium sulfate, filtered and concentrated under vacuum. The residue is purified by flash chromatography on silica gel to provide CT-117147.

EXAMPLE 13

Synthesis of N-(4-chlorophenyl)-6-methylsulfanyl-N'-phenyl-[1,3,5]triazine-2,4-diamine (CT-31888)

A mixture of CT-116433 (108 mg, 0.32 mmol) and sodium methanethiolate (79 mg, 1.13 mmol) in dimethyl sulfoxide (3 ml) was heated at 70° C. for 18 hours. After cooling to room temperature the mixture was diluted with ethyl acetate (25 ml) and was washed with a 1:1 solution of water and saturated aqueous sodium chloride solution (4×25 ml). The organic phase was dried over sodium sulfate, filtered, and concentrated under vacuum. The residue was purified by flash chromatography on silica gel eluting with 5% ethyl acetate-hexane to provide CT-31888 (76 mg, 69% yield). $^1$H NMR ($d_6$-DMSO) δ 7.51-7.60 (m, 4H), 7.26-7.39 (m, 5H), 7.00-7.17 (m, 2H), 2.56 (s, 3H).

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

The invention claimed is:

1. A compound selected from N-benzo[1,3]dioxol-5-yl-6-chloro-N'-(4-chlorophenyl)-[1,3,5]triazine-2,4-diamine, 6-chloro-N-(2,3-dihydrobenzo [1,4]dioxin-6-yl)-N'-phenyl-[1,3,5]triazine-2,4-diamine, N-benzo[1,3]dioxol-5-yl-6-chloro-N'-phenyl-[1,3,5]triazine-2,4-diamine, 6-chloro-N-indan-5-yl-N'-phenyl-[1,3,5]triazine-2,4-diamine, 6-chloro-N-(4-chlorophenyl)-N'-(4-methoxyphenyl)-[1,3,5]triazine-2,4-diamine and 6-chloro-N-(4-chlorophenyl)-N'-phenyl-[1,3,5]-triazine-2,4-diamine, or pharmaceutically acceptable salts thereof.

2. A compound of claim 1, wherein the compound is N-benzo[1,3]dioxol-5-yl-6-chloro-N'-(4-chlorophenyl)-[1,3,5]triazine-2,4-diamine.

3. A compound of claim 1, wherein the compound is 6-chloro-N-(2,3-dihydrobenzo[1,4]dioxin-6-yl)-N'-phenyl-[1,3,5]triazine-2,4-diamine.

4. A compound of claim 1, wherein the compound is N-benzo [1,3]dioxol-5-yl-6-chloro-N'-phenyl-[1,3,5]triazine-2,4-diamine.

5. A compound of claim 1, wherein the compound is 6-chloro-N-indan-5-yl-N'-phenyl-[1,3,5]triazine-2,4-diamine.

6. A compound of claim 1, wherein the compound is 6-chloro-N-(4-chlorophenyl)-N'-(4-methoxyphenyl)-[1,3,5]triazine-2,4-diamine.

7. A compound of claim 1, wherein the compound is 6-chloro-N-(4-chlorophenyl)-N'-phenyl-[1,3,5]-triazine-2,4-diamine.

8. A pharmaceutical composition comprising the compound of any one of claims 1, 2-5, and 6-7 and a pharmaceutically acceptable carrier.

* * * * *